(12) United States Patent  
Thomas et al.

(10) Patent No.: US 8,860,570 B2  
(45) Date of Patent: Oct. 14, 2014

(54) PORTABLE WIRELESS PERSONAL HEAD IMPACT REPORTING SYSTEM

(75) Inventors: Biju Thomas, Dev, CO (US); Timothy Bauer, Denver, CO (US)

(73) Assignee: SenseTech, LLC, Denver, CO (US)

( * ) Notice: Subject to any disclaimer, the term of this patent is extended or adjusted under 35 U.S.C. 154(b) by 223 days.

(21) Appl. No.: 13/366,097

(22) Filed: Feb. 3, 2012

(65) Prior Publication Data

US 2012/0223833 A1    Sep. 6, 2012

Related U.S. Application Data

(60) Provisional application No. 61/439,334, filed on Feb. 3, 2011, provisional application No. 61/510,051, filed on Jul. 20, 2011.

(51) Int. Cl.
| | |
|---|---|
| *G08B 1/08* | (2006.01) |
| *B60Q 1/00* | (2006.01) |
| *B60R 25/10* | (2013.01) |
| *H04M 11/04* | (2006.01) |
| *H04B 7/00* | (2006.01) |
| *H04W 24/00* | (2009.01) |
| *G08G 1/123* | (2006.01) |
| *G08B 21/04* | (2006.01) |
| *G06F 19/00* | (2011.01) |

(52) U.S. Cl.
CPC .......... *G06F 19/3418* (2013.01); *G06F 19/345* (2013.01); *G08B 21/0446* (2013.01)
USPC . 340/539.12; 340/436; 340/438; 340/426.16; 455/404.2; 455/41.2; 455/456.1; 701/533

(58) Field of Classification Search
USPC ............ 340/539.12, 436, 438, 573.1, 426.16, 340/539.26, 539.13; 455/404.2, 41.2, 455/456.1, 457, 427, 345; 701/533, 433, 701/431, 410
See application file for complete search history.

(56) References Cited

U.S. PATENT DOCUMENTS

| 7,289,786 B2 * | 10/2007 | Krasner ...................... 455/404.2 |
| 7,656,286 B2 * | 2/2010 | Benson et al. ................ 340/508 |
| 7,904,053 B2 * | 3/2011 | Krasner et al. ............. 455/404.2 |

(Continued)

OTHER PUBLICATIONS

Funk et al., "Validation of Concussion Risk Curves for Collegiate Football Players Derived from HITS Data," *Annals of Biomedical Engineering*, (2012), 40(1):79-89.
Ivancevik, V.G., "New mechanics of traumatic brain injury," *Cogn Neurodyn*, (2009), 3:281-293.

(Continued)

*Primary Examiner* — Jennifer Mehmood
*Assistant Examiner* — Mirza Alam
(74) *Attorney, Agent, or Firm* — Dorsey & Whitney LLP

(57) ABSTRACT

A system for sensing, analyzing and reporting a collision event experienced by a person or object sensor module designed to a person or object, module angular velocities over time and a processor for analyzing the sensed velocities, calculating properties of angular velocities, such as jerk and jolt, comparing these properties with threshold values selected to correlate to predicted severities of injury to the person or object, transmitting information regarding these properties to communication device user-designated persons. Also provided are group tracking and communication devices for use by monitors to manage multiple persons equipped with sensor modules. The sensor modules and group tracking and communication devices are designed to be portable, attachable and detachable so that they can be attached to different types of gear used by persons engaging in different activities.

80 Claims, 23 Drawing Sheets

(56) References Cited

U.S. PATENT DOCUMENTS

| | | | |
|---|---|---|---|
| 8,085,144 B2* | 12/2011 | Appelt et al. | 340/539.11 |
| 8,284,100 B2* | 10/2012 | Vartanian et al. | 342/357.3 |
| 8,396,485 B2* | 3/2013 | Grainger et al. | 455/456.1 |
| 8,421,617 B2* | 4/2013 | Kaminski et al. | 340/539.13 |
| 8,463,545 B2* | 6/2013 | Boore et al. | 701/533 |
| 8,665,087 B2* | 3/2014 | Greene et al. | 340/539.13 |
| 2008/0012761 A1* | 1/2008 | Derrick et al. | 342/357.07 |
| 2008/0186161 A1* | 8/2008 | Fussner et al. | 340/539.13 |
| 2010/0120362 A1* | 5/2010 | Walley et al. | 455/41.2 |

OTHER PUBLICATIONS

Margulies et al., "A Proposed Tolerance Criterion for Diffuse Axonal Injury in Man," *J. Biomechanics*, (1992), 25(8):917-923.

Rowson et al., "Linear and Angular Head Acceleration Measurements in Collegiate Football," *Journal of Biomechanical Engineering*, (2009), 131:061016-1-061016-7.

Rowson et al., "Rotational Head Kinematics in Football Impacts: An Injury Risk Function for Concussion," *Annals of Biomedical Engineering*, (2012), 40(1):1-13.

* cited by examiner

US 8,860,570 B2

PORTABLE WIRELESS PERSONAL HEAD IMPACT REPORTING SYSTEM

CROSS-REFERENCE TO RELATED APPLICATIONS

This application claims priority based on prior Provisional Application No. 61/439,334, filed Feb. 3, 2011 discloses related subject matter and is incorporated herein by reference to the extent not inconsistent herewith. Any information or definitions inconsistent with those disclosed herein are specifically not incorporated by reference.

This application claims priority based on prior Provisional Application No. 61/510,051, filed Jul. 20, 2011 discloses related subject matter and is incorporated herein by reference to the extent not inconsistent herewith. Any information or definitions inconsistent with those disclosed herein are specifically not incorporated by reference.

STATEMENT REGARDING FEDERALLY SPONSORED RESEARCH

Not Applicable.

APPENDICES

1. Copy of U.S. Provisional Application No. 61/439,334, filed Feb. 3, 2011.
2. Copy of U.S. Provisional Application No. 61/61/510,051, filed Jul. 20, 2011.
3. Ivancevik, V. C. (2009), "New Mechanics of Traumatic Brain Injury," Cognitive Neurodynamics 3(3):281-293, incorporated herein by reference to the extent not inconsistent herewith.
4. Rowson, S. et al. (2009), "Linear and Angular Head Acceleration Measurements in Collegiate Football," J. Biochemical Engineering 131(6):061016, incorporated herein by reference to the extent not inconsistent herewith.
5. Margulies, S. S. et al. (1992), "A Proposed Tolerance Criterion for Diffuse Axonal Injury in Man," J. Biomechanics Vol. 25, No. 8, pp. 917-923, incorporated herein by reference to the extent not inconsistent herewith.
6. Funk, J. et al. (2012), "Validating Concusion Risk Curves for Collegiate Football Players Derived form HITS Data," Annals of Biomedical Engineering, Vol. 40, No 1, 79-89, incorporated herein by reference to the extent not inconsistent herewith.
7. Rowson, S. et al. (2012), Rotational Head Kinematics in Football Impacts: An Injury Risk Function for Concussion," Annals of Biomedical Engineering, Vol. 40, No 1, 1-13, incorporated herein by reference to the extent not inconsistent herewith.

DESCRIPTION

This disclosure generally pertains to sensing devices worn or carried by individuals and arranged to provide sensing, measuring, recording, analyzing and reporting of one or more desired variables, including collision impacts, biometric data, climatic data, percussive, sonic and vibrational forces, the presence of toxic substances such as poisonous gases, nerve agents and bioweapons, along with oxygen levels. The sensing devices are specifically configured to employ mobile communications devices to report the sensor data and more specifically to store and analyze the data and alert selected recipients in the case of an impact collision above a certain threshold, or in the case of, for example, other adverse biometric, climatic, atmospheric or battlefield conditions. The system is also designed to store and collect such data for research and development.

Every day millions of people engage in activities where their bodies are exposed to collision impacts of varying intensity. It is generally recognized that higher intensity collision impacts present severe risks for the human body, resulting in injuries that range from nominal to serious and deadly. But, numerous injuries, some leading to death, also occur at very low levels of impact. Diffuse axonal injury (DAI) and related low level injuries are not readily noticeable in most cases by simply surveying damage to headgear or the person. Most collision measuring devices only measure direct line acceleration and do not measure rotational acceleration and/or deceleration.

An example of protective headgear, such as helmets, outfitted with devices to sense shock or impact is the Head Impact Telemetry System (HITS), commercially available from Simbex, LLC, of Lebanon, N.H. The HITS is a helmet impact sensing and telemetry system used to monitor American football players.

One of the drawbacks of such conventional, helmet-based impact sensing systems is non-portability of the devices due to integration into the fabricated body of the protective headgear or complicated distribution of multiple impact sensing devices within the protective headgear, resulting in reduced user ability to transfer the impact reporting system between the specialized headgear for different activities. A user may participate in any number of different activities where activity-specific protective headgear or other protective gear is used e.g., steel working, snowboarding, horse riding, and bicycling; a great deal of time must be consumed by having to disassemble the complicated array of impact sensing units after each use so that the impact reporting device can be used with another piece of protective headgear. Further, it is cost-prohibitive to outfit each helmet with a separate, unique impact-sensing device when only one helmet is being used at a time. These systems also require a team of specialists to parse and make sense of the collected data.

DAI is a type of brain injury caused by traumatic shearing forces that occur when the head is rapidly accelerated or decelerated, usually from rotational forces due to severe deceleration. DAI occurs when different parts of the brain slide over other tissue (e.g. brain movement relative to the skull or other anatomical sub-parts of the brain as a result of rapid rotational acceleration and/or deceleration) disrupting axons and the neural processes that allow one neuron to communicate with another. Rotational acceleration and deceleration, as opposed to straight-on impact collisions, cause the shear and strain stress of the brain tissue and in some cases can cause the brain to rotate inside the skull that can shear blood vessels, causing bleeding. Because different parts of the brain have different tissue densities and distances from the axis of rotation, the rotation of different parts of the brain, due to different tissue densities, can cause even sub-clinical, mild DAI that can have long lasting effects and lead to permanent disability. Sometimes DAI is caused by angular jolt, which is derived from angular velocity over time (angular jolt=inertia moment×angular jerk). When there is a DAI, it is important to call for emergency help or follow up to minimize the harm to the injured individual.

There are two additional problems commonly associated with collision impacts incurred by humans. First, an injured individual often does not or cannot recognize the intensity of an impact or the risk associated with the impact they suffered. For example, a person may sustain an impact collision without realizing that it was severe enough to cause a concussion or DAI, and they will often dismiss the incident because they are not immediately experiencing the overt symptoms of brain injury or concussion. Second, when an individual sustains debilitating impact while they are isolated and there is no one around to summon or administer assistance, there is substantial risk of worsening of the injury and/or death.

Head and or body impact collisions sustained during sports and other recreational, vocational and military physical activities pose a considerable risk of injury, or even death, to an individual. For example, according to the Consumer Product Safety Commission, there were over 450,000 sports related head injuries in the US in 2004. Injuries incurred during bicycling, baseball and football made up the majority of hospitalizations due to head injury.

Additionally soldiers on the battlefield are subject to not only incurring DAI, but also a wide array of other adverse conditions such as bioweapons, poisonous gases, nerve agents, explosives and their sonic and concussive effects, extreme climatic conditions and numerous other hazards.

This disclosure is directed to activities where individuals, groups of individuals, and those responsible to monitor them, engaged in activities with risk of the occurrence of collision events, recognize that they are at risk of sustaining an injurious impact, and/or other adverse conditions. When there is an impact, or other adverse conditions of sufficient intensity, the sensing devices hereof are configured to provide notification of such to the individuals and/or their monitors. In embodiments, the devices hereof employ a wireless radiofrequency (RF) Bluetooth, Bluetooth Low Energy or other Low Energy technology wireless transmitter, e.g. ANT+, Zigbee, or others known to the art, to communicate the impact or adverse conditions to the individuals' and or monitor's mobile communications device. In embodiments, this communication is processed and triggers an alarm on the mobile communications device, and if the individual does not locally respond to the alarm, the mobile communications device is programmed to summon assistance and communicate the individual's location.

There is a need in the art for a system that is sensitive enough to measure slight impacts and also capable of measuring different types of impacts such as those caused by rotational acceleration and deceleration. Accordingly, the present disclosure provides a portable diagnostic sensing and reporting system and in an embodiment a head impact sensing and reporting system which measures angular velocity and G-forces in 3 axes and direct accelerations and decelerations, for use with protective headgear and helmets, such as used during bicycling, skiing, motor sports, recreational, vocational and military physical activities, to determine and record real time data such as the magnitude of direct and rotational head impacts and positional information for research, activation of emergency medical services, personal, and third-party purposes.

Soldiers on the battlefield are subject to a wide array of adverse conditions. Often, they are too busy or overwhelmed to deploy sensors and analyze the sensed data. There is a need for a remote monitor, who is not under the direct heat of battle, to assess the battlefield conditions in order to make appropriate decisions and balance the strategic needs with the soldier's health. Therefore, this disclosure also provides a way to measure adverse conditions which occur on a battlefield, such as sonic, percussive and concussive forces, the presence or absence of toxic agents such as poisonous gases, nerve agents, bioweapons, climatic conditions and biometric data. Additionally, emergency responders and others for whom oxygen levels are a concern, such as miners, pilots and scuba divers would also benefit from sensors which measure oxygen levels, in the case of, for example, firemen in a burning building.

Many sensing units are large, cumbersome and unable to be transferred between different items of equipment worn or carried by users at risk of impact injury. This disclosure provides a sensing and reporting system which is small enough to be portable and easily handled, and which is easily transferrable, and removably attachable to different items of equipment or clothing.

Many sensing units are not designed for the at-home user or those without special training, however, this disclosure illustrates a consumer friendly item calibrated and designed to be understood and used by an average, non-specialized user.

Often people who incur brain trauma are either not immediately aware of that fact, or are unconscious and unable to call for help or report their position. In light of this fact, the present disclosure explicates a portable diagnostic sensing and reporting system which senses and reports head impact collisions, and other sensed information if desired, and alerts emergency medical services, and other desired recipients. When an individual experiences an adverse condition and is unconscious or otherwise unable to respond to a message, the system pinpoints their location and sends a signal to emergency medical services or other recipients. On the battlefield and other vocational and recreational conditions a wide variety of sensors can be employed as well as locating systems which allow for one or more monitors to track numerous soldiers or wearers.

Many models designed to predict the likelihood of injury from adverse conditions are inexact due to the lack of a database with a large amount of stored information on the effects of sensed conditions on various types of individuals. Hence, the disclosure provides a method of predicting the type and severity of an injury resulting from a collision event comprising collecting information for a database consisting of data collected from other collision events and/or adverse conditions involving the same and/or other persons, including demographic information, and measured parameters of the impact, as well as the type and severity of the resulting injury, and correlating the severities and types of injuries with the other parameters in order to predict the type and severity of injury an injury resulting from a new collision event whose parameters are measured by the present system.

Methods of making and using the sensing systems described herein are also provided.

Additionally, firmware that runs on the sensor modules and/or group communication devices hereof, which filters raw data, does preliminary calculations provides a time sequence, and sends the data to a wireless interface for data transmission is needed and is provided herein.

Methods of making and using databases comprising demographic data correlated with type and severity of injuries are also provided, as are electronic storage media having such databases stored therein, such electronic storage media including CDs, flash drives, computers and other electronic processing and storage devices known to the art.

BRIEF DESCRIPTION OF THE DRAWINGS

FIG. 15 shows schematics for components of a Bluetooth Low Energy to Classic Converter (BLEC) hereof.

FIG. 16 shows schematics for components of a Bluetooth Enabled Gyroscope with Accelerometer (BEGA) hereof.

DEFINITIONS

Figure 1:
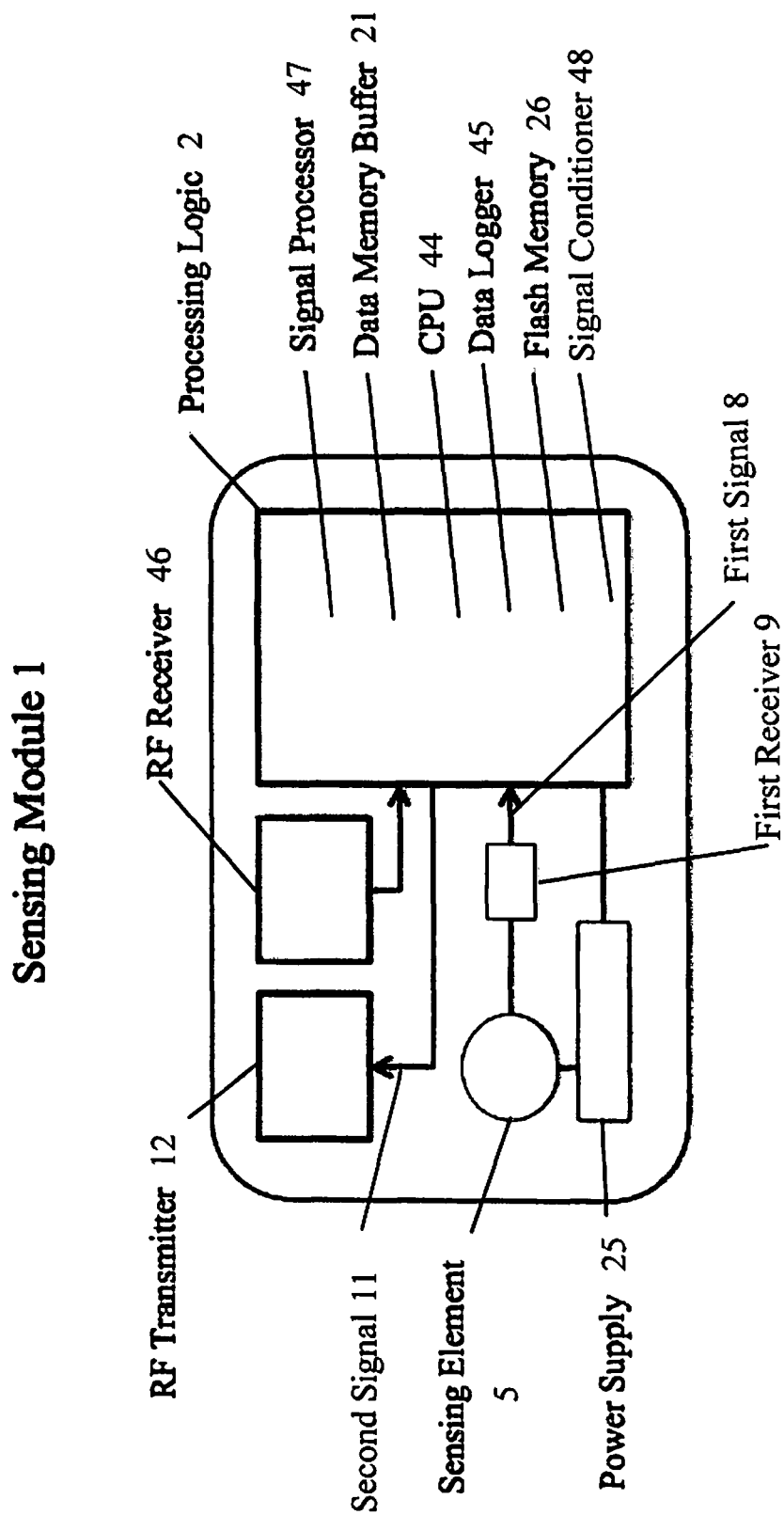
FIG. 1 illustrates components of a sensor module hereof.

A collision event as used herein is an event causing an impact on a person or object of another person or object. The impacting object can be a solid, liquid, e.g. a wave of water, or gas, e.g., a strong wind or force from an explosion.

An accessory as used herein refers to an object carried or worn by a person, such as an article of clothing, hat, protective gear, key fob, jewelry, backpack, and the like. The sensor module and/or the group tracking and communication device hereof are, in embodiments, configured, such as with attachment means or by being formed integrally with the accessory, to travel with the person and experience the impact of collision events experienced by the person.

Angular Velocity refers to a vector quantity (more precisely, a pseudovector) which specifies the angular speed of an object and the axis about which the object is rotating. It is sometimes also called rotational velocity and its magnitude is called rotational speed, and typically measured in cycles or rotations per unit time (e.g. revolutions per minute).

Angular acceleration and deceleration refer to the rate of change of angular velocity.

Angular Jerk as referred to herein is a derivative of angular velocity over time. Jerk means shaking the object's (e.g., head's) own mass-inertia matrices (mainly in the atlanto-occipital and atlanto-axial joints.) For example, while driving a car, the jerk of the head-neck system happens every time the driver brakes abruptly. See Ivancevik, V. C. (2009), "New Mechanics of Traumatic Brain Injury," Cognitive Neurodynamics 3(3):281-293, incorporated herein by reference to the extent not inconsistent herewith.

Angular Jolt as referred to herein is derivative of angular momentum over time. It is an impulsive loading that strikes the head in several coupled degrees-of-freedom simultaneously. 'Jolt' means actually hitting the head with some external mass-inertia matrices included in the 'hitting' SE(3)-jolt, or hitting some external static/massive body with the head (e.g., the ground-gravitational effect, or the wall inertial effect). See Ivancevik, V. C. (2009), supra.

Burst data stream refers to a short, non continuous series of sequential data.

Differentiator refers to a component for determining multiples of the time derivatives of accumulated angular velocity signals over a predetermined period of time.

Integrator refers to a component for computing a cumulative summation of force data over a particular period of time.

3-axis accelerometer refers to a device that measures linear forces in three axes.

DAI stands for "diffuse axonal injury," a type of brain injury caused by shearing forces that occur between different parts of the brain as a result of changes in rotational velocity, acceleration, jerk and jolt.

RF stands for radio-frequency.

SPOT refers to a portable satellite communication device.

MEMS stands for micro-electric mechanical system.

EEPROM stands for an electrically erasable programmable read-only memory.

BLE stands for Bluetooth Low Energy.

BLEC stands for Bluetooth Low Energy to Classic Converter.

BEGA Bluetooth Enabled Gyroscope with Accelerometer.

Cloud computing as used herein means using multiple server computers via a digital network, as though they were one computer.

Program and Programmed as used with respect to processors herein have their ordinary meaning in the art and can include sequences of steps encoded in hardware, software or firmware.

Signal communication between components hereof refers to the use of any known means for transmitting signals from one device to another, such as via RF, cable or other known types of signals.

DETAILED DESCRIPTION

The following description of various specific embodiments is exemplary in nature and is in no way intended to limit the scope of the claims hereof. In embodiments, art-known equivalents of exemplified components, materials and method steps can be substituted for those specifically described herein and these embodiments are considered to fall within the scope of the claims. This disclosure encompasses embodiments including less than all the components, materials and method steps of embodiments specifically described herein.

Provided herein is a system for sensing and reporting a collision event of a person or object with another person or object, said system comprised of a sensor module 1 with a sensor unit processor 2, a group tracking and communication device 3, and a mobile communication device 4 FIG. 1.

Figure 2:
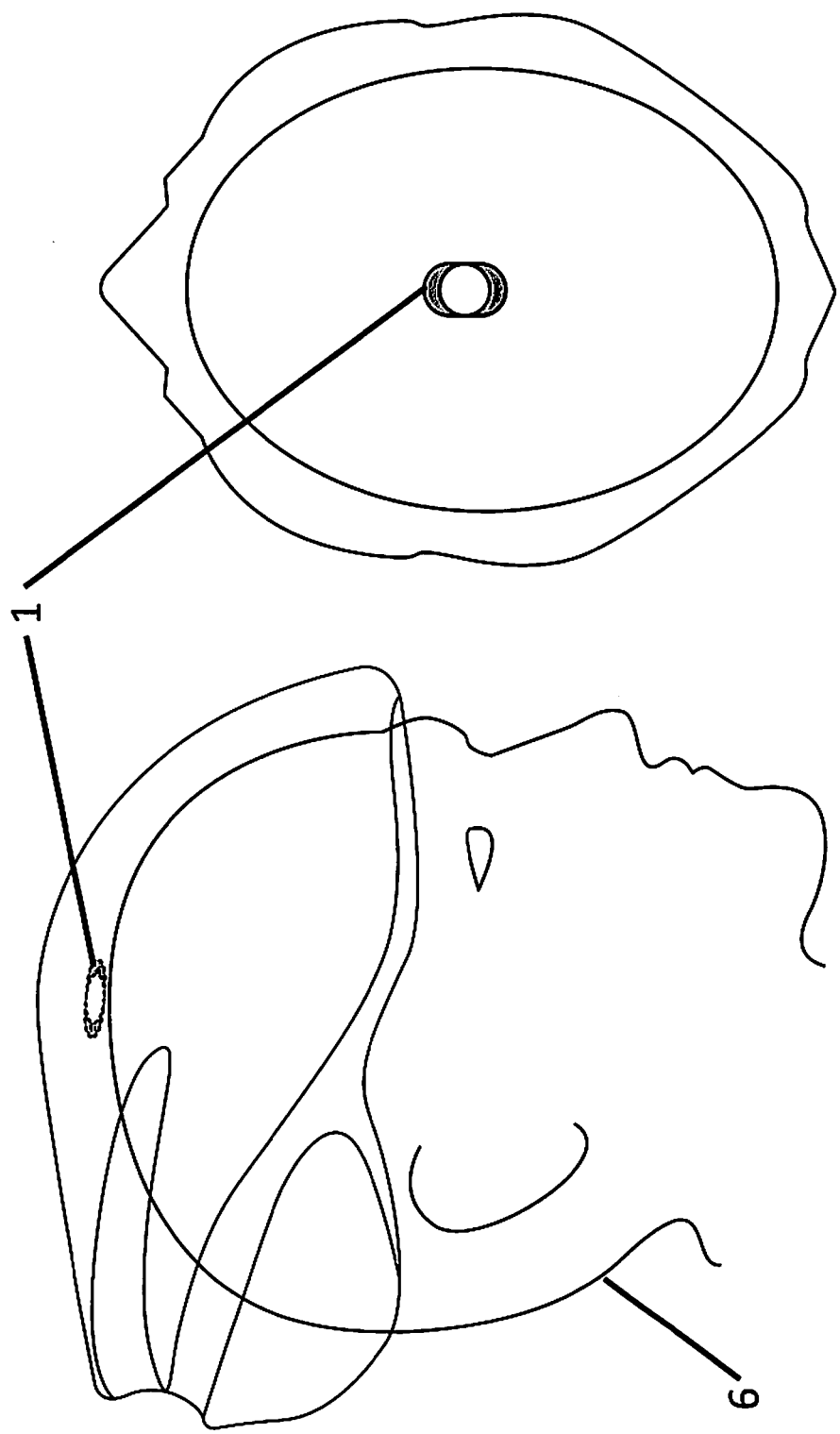
FIG. 2 illustrates placement of sensor modules arranged on a bicycle helmet.
Figure 4:
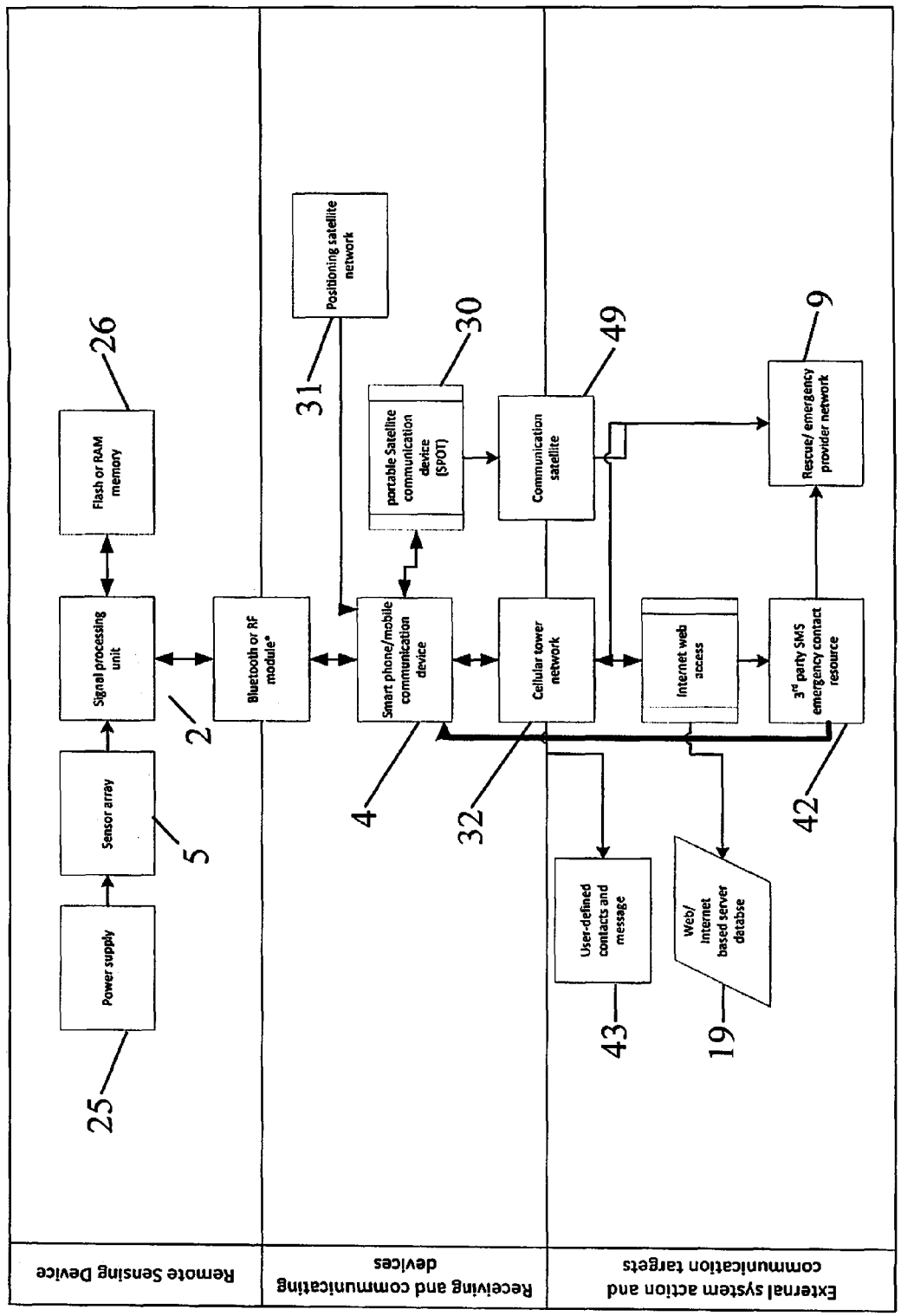
FIG. 4 Illustrates the flow of signals from a sensing and reporting system (top level, through receiving and communicating devices (middle level) to external action and communication targets (bottom level).

The sensor module 1 consists of at least one sensor 5 operationally connected to one or more persons or objects 6 FIG. 2, which is capable of sensing angular and/or direct velocity of a person or object 6 over time as a result of a collision event 7 and of producing first signals 8 FIG. 4, comprising information representing properties of direct and angular velocity over time.

Figure 3:
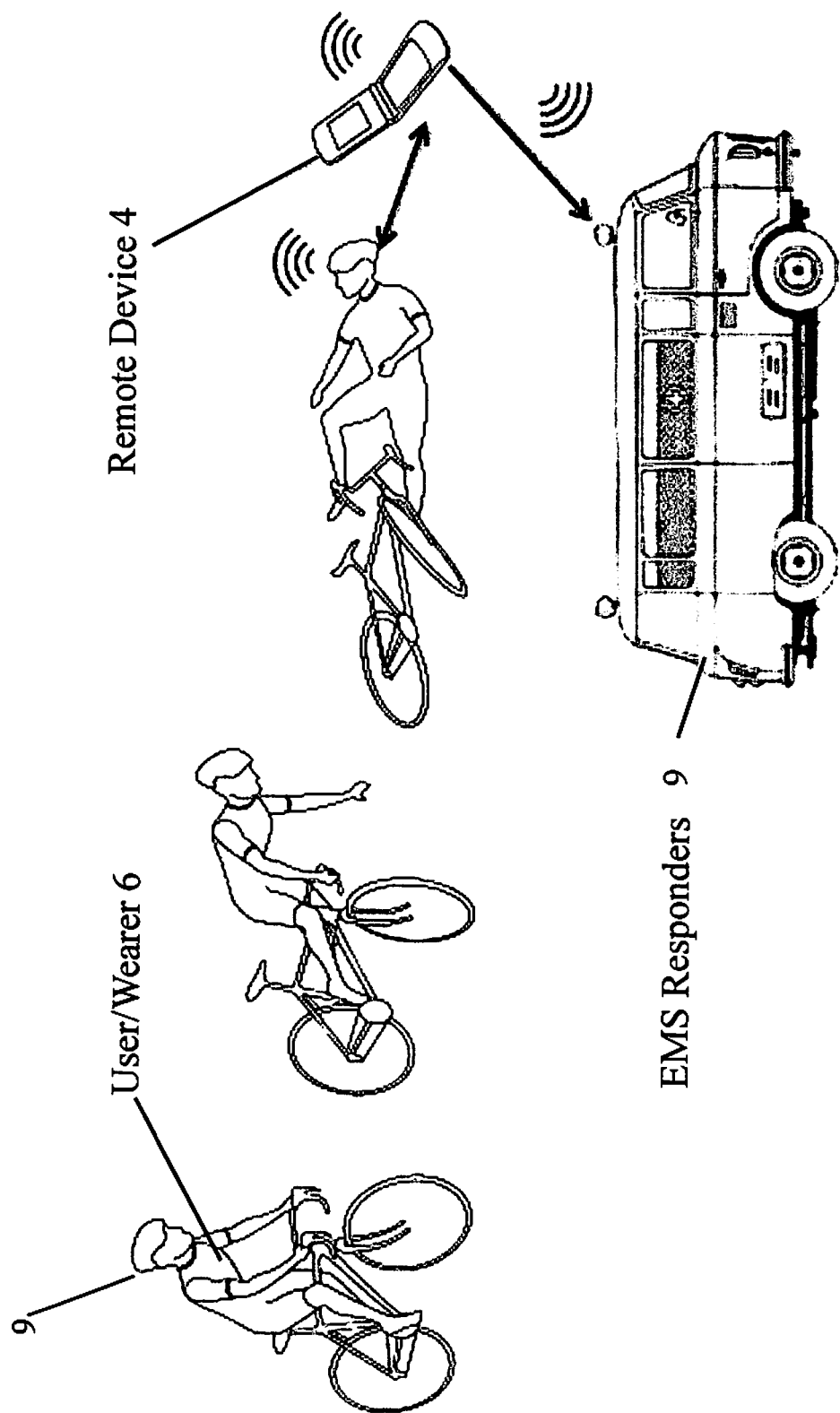
FIG. 3 illustrates a signal path from a fallen bicycle user's sensor module to a remote device to emergency service providers.

The sensor module 1, the group tracking and communication device 3, and the mobile communication device 4, are communicatively configured to allow the signal transmission to emergency service responders 9 FIG. 3.

The sensor module processor 2 is in signal communication with the sensor 5 via a first receiver 10 FIG. 1 and is programmed to analyze sensor information and compare it to one or more preset threshold values indicative of the severity of collisions to produce a second signal 11 FIG. 4, consisting of data representing the results of said comparison(s). In embodiments, the processor 2 converts raw analog signals from gyroscope and accelerometer components (sensors 5) to digital signals and also runs a program that filters the raw data, performs preliminary calculations, gives the data a time sequence, and sends the data to a wireless interface 12 for data transmission to an external device 4, e.g., a cellular telephone or tablet computer, which can be a group tracking 3 and communication device 4.

The numerical threshold values of the data from the sensor 5 cause the processor 2 to generate a message to alert the user 6 that he or she has experienced a collision event 7 and should take a recommended action, depending on the predicted severity of injury caused by the collision event, such as seeking medical attention. The processor 2 can also automatically call emergency response personnel 9 if the predicted injury is severe, or if the user fails to respond to the alarm signal sent by the processor 2 FIG. 3.

The portability and small size of the sensor module 1 (a cylinder approximately 2 cm in diameter and 0.5 cm high) are further advantages of the system disclosed herein.

Figure 6A:
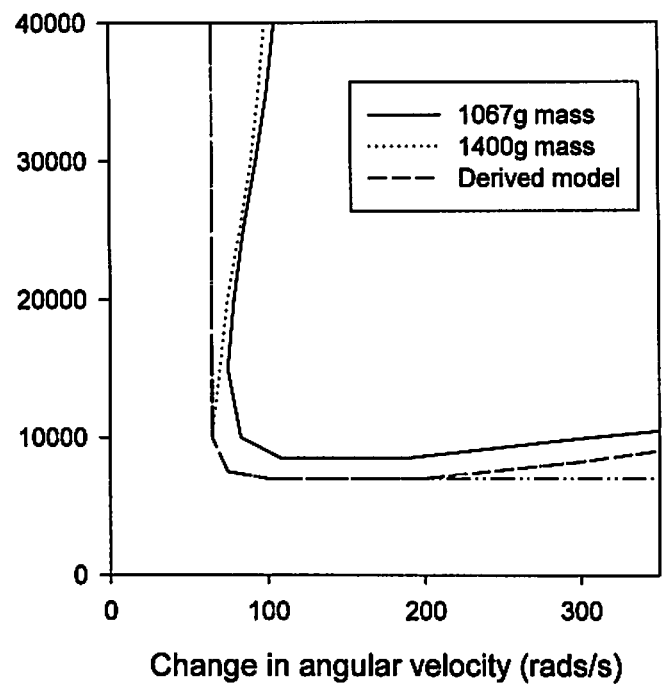
FIG. 6(a) shows modeled data from Margulies et al. of angular velocity and acceleration threshold values for two different brain masses and derived model fit for DAI threshold detection.
Figure 6B:
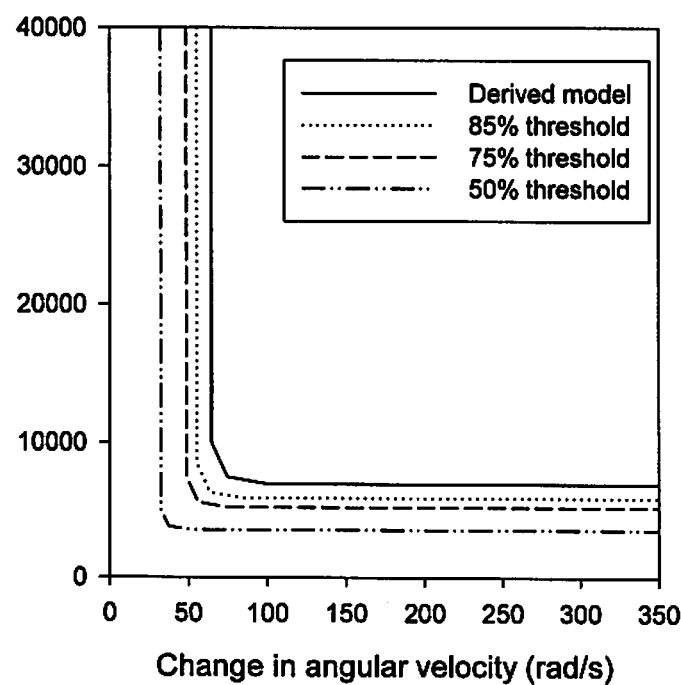
FIG. 6(b) shows derived threshold model for 100% threshold for DAI (derived model) and examples of threshold models as functions of the derived model (E.g. 85% of derived model, 75% of derived model, etc) are provided as levels of thresholds to be utilized in the injury detection algorithm.

High forces impacting a user over a short period of time have greater potential for injury of the user, and an accumulation of such high impact forces over time also affect the severity of injury likely to be caused by a collision event (see, e.g., Margulies, S. S. et al. (2009). In an embodiment hereof, the threshold values are calculated from a relative percentage of collected data for known levels of DAI resulting from angular velocity (x axis) and angular acceleration (y-axis) or vice versa FIG. 6(*a*). In a simple form, the impact data from scientific literature and other known sources are fit using nonlinear regression to the equation:

$$y = e^{-x}$$

Available literature of human head impacts are documented for collegiate and professional American football players. Information regarding the forces of head impact and resulting risk for concussion for these highly trained athletes have been defined with particular importance to rotational forces acting upon the head and brain. However, little human data exist or injury thresholds determined for persons not specifically trained for high impact sports, in particular for other age and demographic groups. To establish these injury thresholds, a series of threshold levels e.g., $y = e^{-c \times 1.0}$; where c is a constant for the x axis offset at 100% of the absolute DAI threshold) from known scientific literature are used (see, e.g., Margulies, S. S. et al. (2009); Rowson, S. et al. (2012)). A matrix of models are computed to determine separate thresholds FIG. 6(*b*). For example, one embodiment uses the 50% rule, where $X_{0.5}$ and $C_{0.5}$ reflect the x values and constant offset at 50% of the known absolute DAI threshold (e.g., $y = e^{-c}0.5^x 0.5$). Different relative percentages are used for different populations (e.g. children) where maturation of the brain, skull (and skull density), and total head mass relative to body mass are used to adjust the sensitivity and specificity of the threshold for determining clinically significant events. More complex equations and models are applied as real (human) data are obtained to populate the data sample and as knowledge in this field grows. Examples include:

$$f(x) = ab^x x^c + \varepsilon$$

$$f(x) = \frac{(ae^{bx})}{x + \varepsilon}$$

$$f(x) = \frac{b + (a-b)}{(1 + 10^{(c-x)})}$$

and, where $$x = \frac{a\_x + t^{(bx)}}{(1 - c_x)}$$

$$y = \frac{a_y + t}{t^{(by)} - c_y}$$

Other examples of data normalization, using Weibull, Rician, or other statiscal distributions maybe performed to fit the data.

Figure 13A:
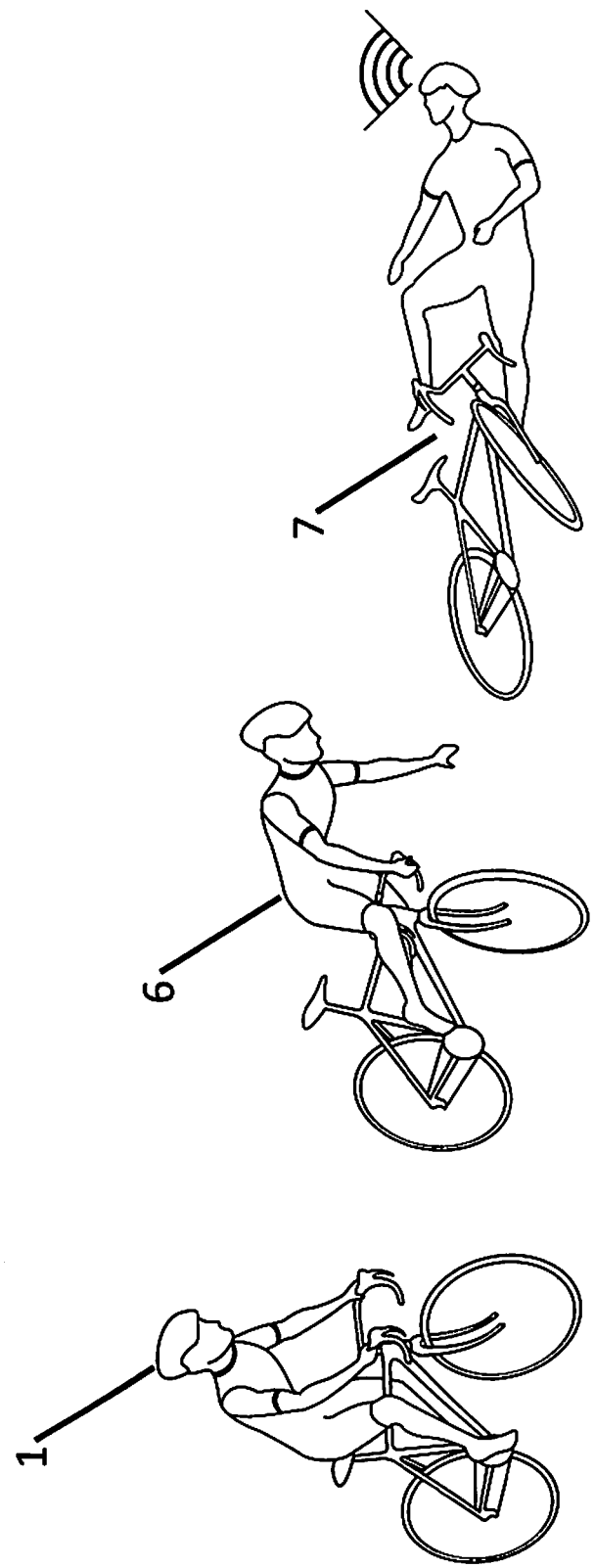
FIG. 13(a) illustrates a fallen user out of range of a communication device.
Figure 13B:
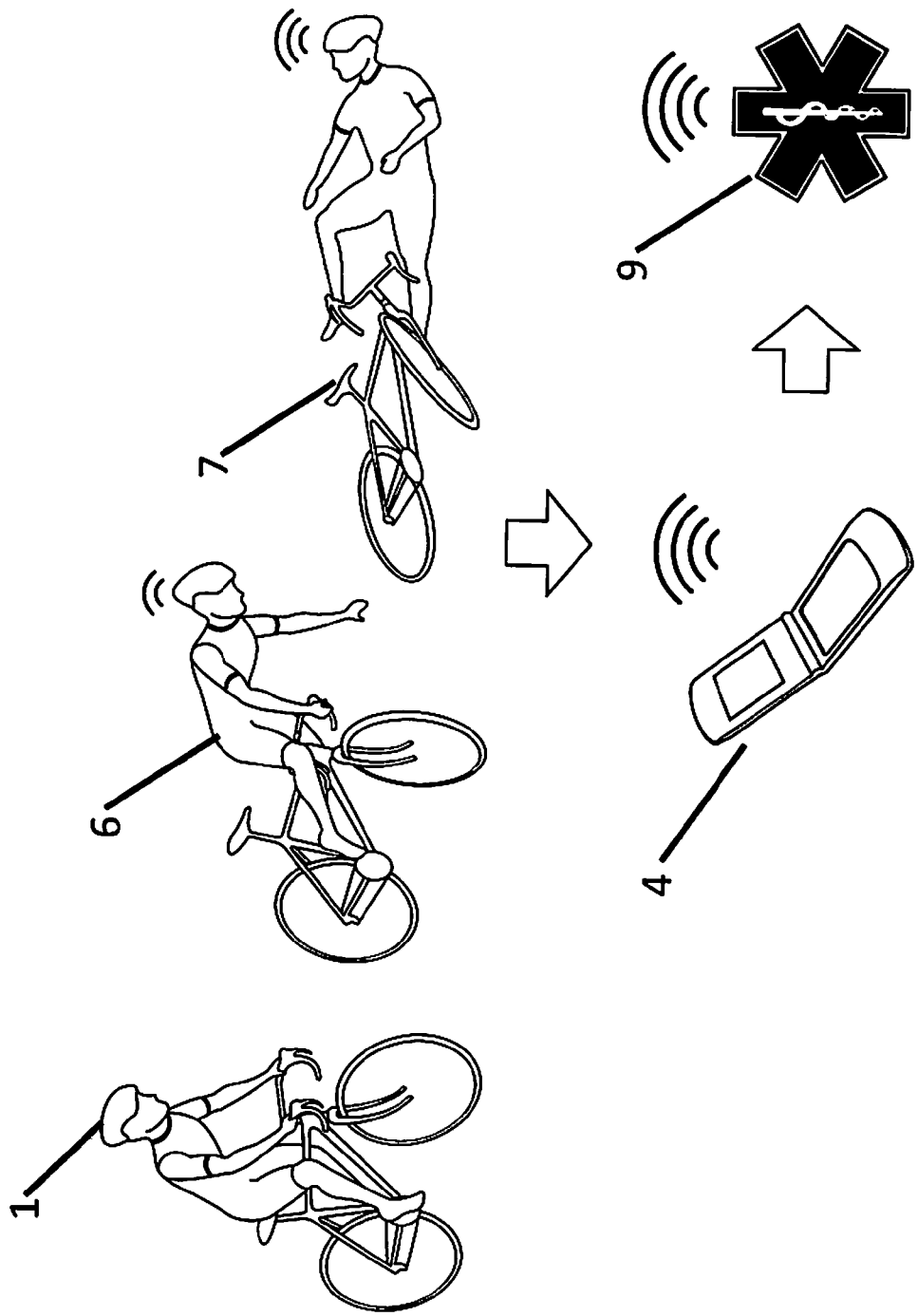
FIG. 13(b) illustrates a fallen user in range of a communication device.
Figure 14:
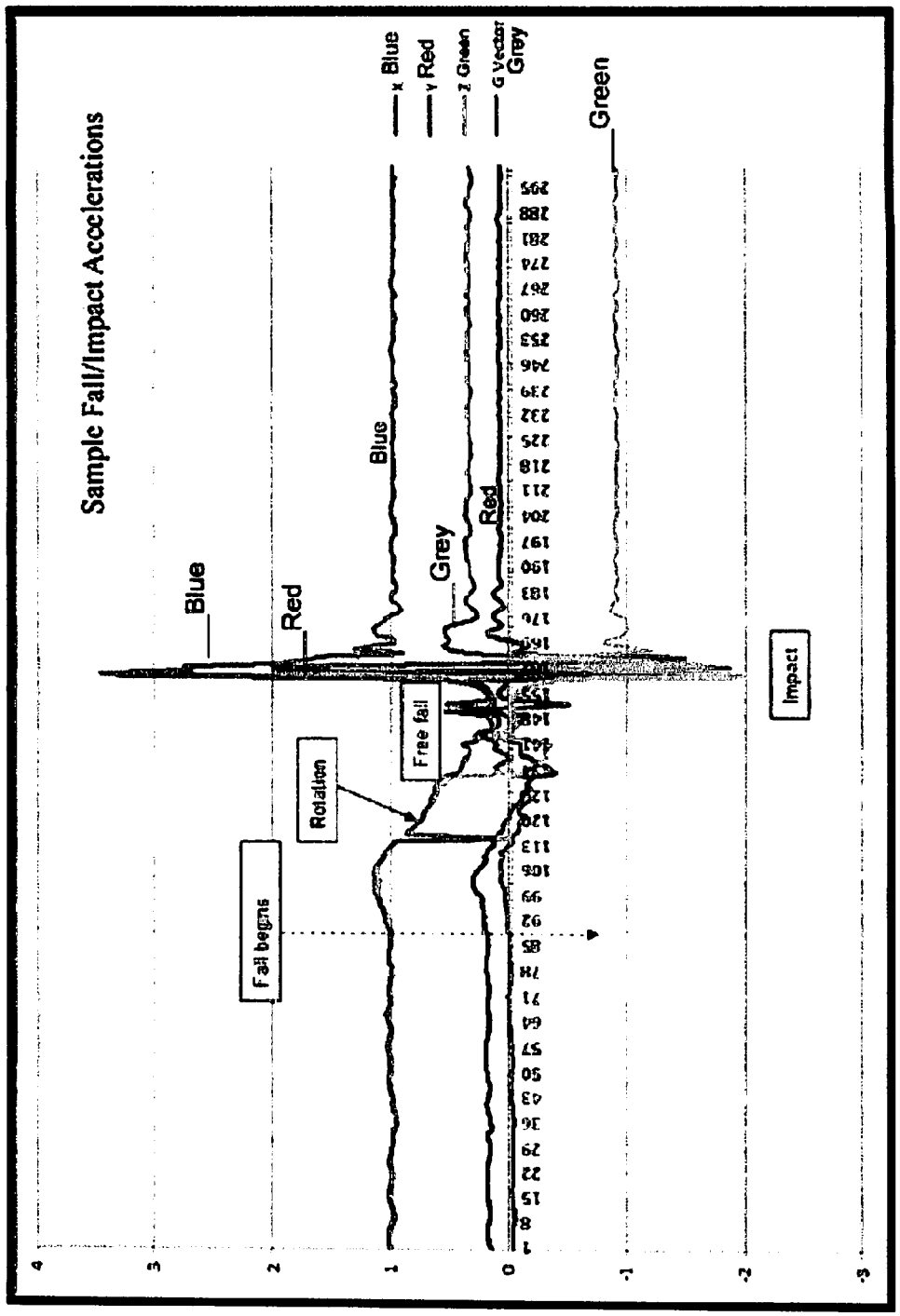
FIG. 14 is a graphical representation of acceleration profiles generated during a fall and impact.

FIG. 13 shows sample linear accelerations associated with a fall impact.

The first receiver is or comprises a component selected from the group consisting of a mobile communication device, a processor, an internet terminal, or other electronic device capable of receiving a signal FIG. 4.

Figure 7:
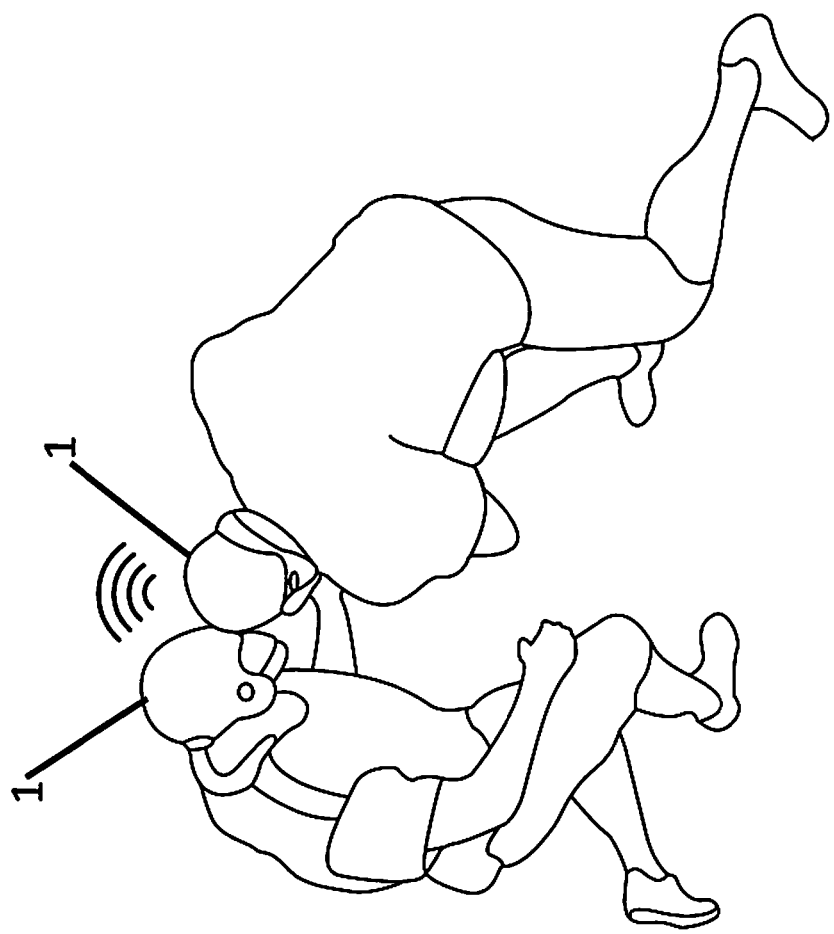
FIG. 7 illustrates a coach employing the group tracking and communication device to monitor sensor modules worn by a group of athletes.
Figure 7:
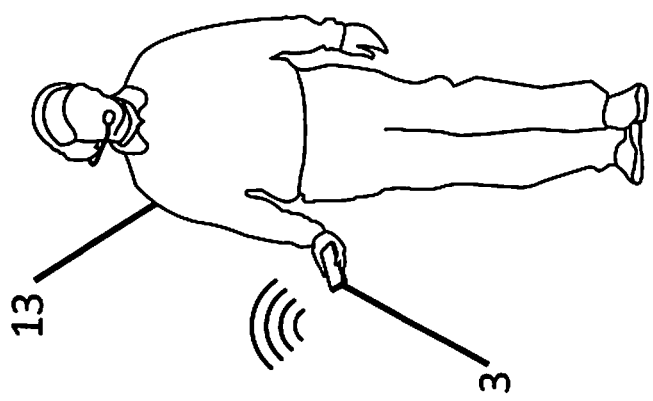

The group tracking and communication device 3 allows a monitor 13, such as a coach, parent, teacher or military observer, to receive messages from sensors attached to multiple players, children, students or soldiers FIG. 7 and for messages to be sent to multiple receivers (emergency responders, designated people, servers, and other interested persons) or to signal receivers 4 such as smart telephones, computer tablets and other portable communication devices 4. The group tracking and communication device can be configured as integral or separate device from the sensor module 1.

Figure 5:
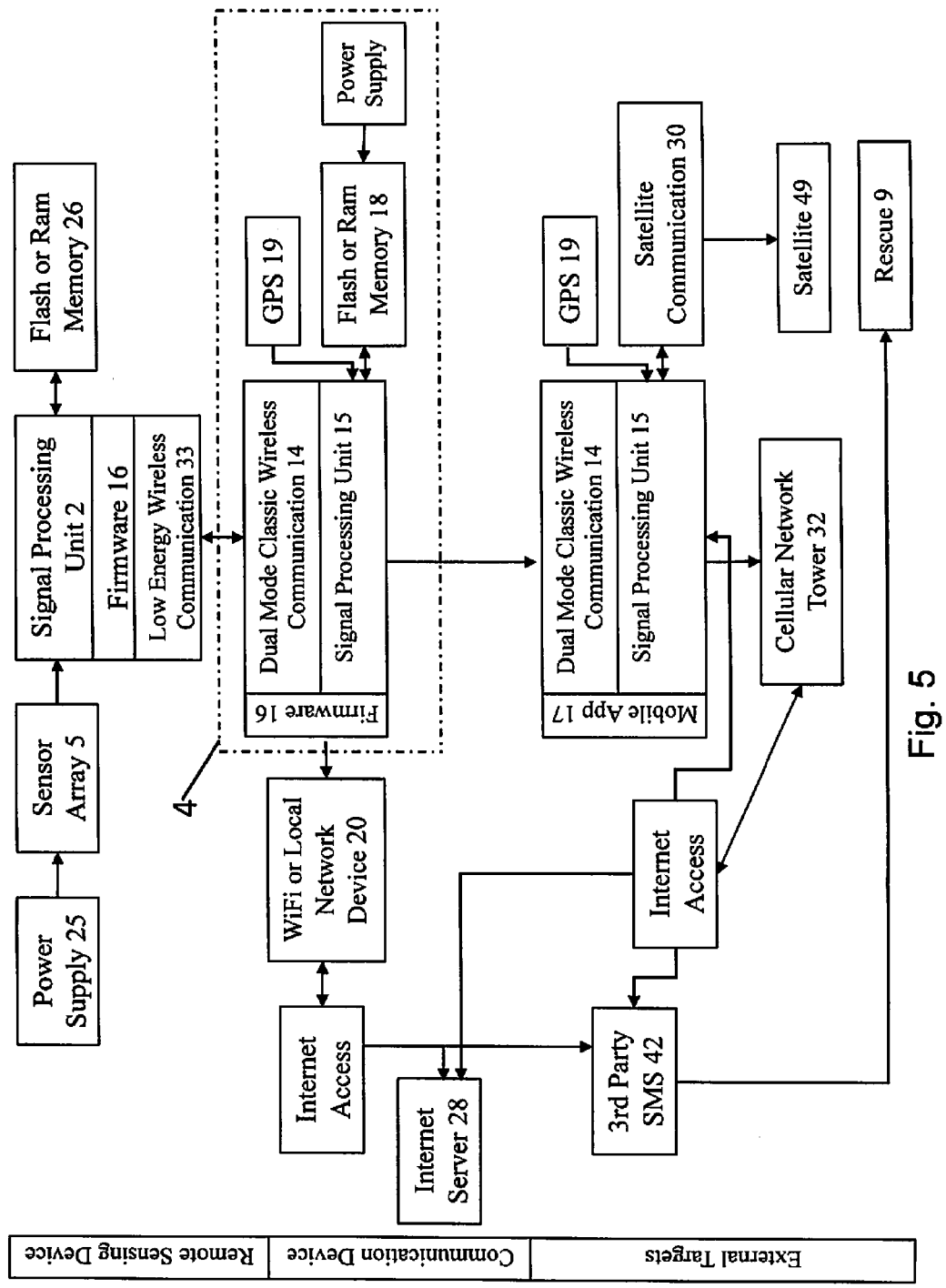
FIG. 5 illustrates a system as shown in FIG. 4 with the addition to the middle level of a group tracking and communication components (enclosed in dotted lines).

The group tracking and communication device comprises a second receiver 14 for receipt of signals from the sensor module processor 2 FIG. 5, is attached to one or more people or objects 6 and comprises a processor 15 programmed to send signals to various receivers 4. In one embodiment, the group tracking and communication device connects directly to the Internet FIG. 5. The group tracking and communication device is responsible for communication between the sensor module processor 2 firmware 16 and another communication device such as the user's cellular telephone 4 (generally a smart telephone programmed with applications 17 for receiving and sending the signals and messages described herein) FIG. 5. The processor of the group tracking and communication device 3 has the capability of storing data in its flash memory 18 and can have its own GPS sensor 19, as well as a Wi-Fi interface 20 and antennae for direct-to-Internet communication FIG. 5. This processor 15 can be programmed to compare the data from the sensor to threshold values to determine if a collision event 7 occurred and send the data to the other communication device 4 (e.g., the user's cellular telephone), or to an internet receiver via Wi-Fi signals.

The mobile communication device 4 comprises a device such as a smart telephone or tablet computer with Internet connectivity, capable of receiving signals and transmitting messages FIG. 4. In embodiments, it is programmed to handle all communication between itself, the group communication device 4 and/or the sensor module 1 and external systems to communicate information and report back. Such information can include data about the user 6, such as biological parameters (e.g., blood pressure, temperature, and movements), and demographic information about the user (e.g., age, weight, medical insurance, and the like). Devices for measuring biological parameters are known to the art and can be easily adapted to the present system by one of ordinary skill in the art. For example, piezoelectric or similar sensing units configured into a head band or head liner and position on the user's temples can monitor and transmit electroencephalogram (brain wave) and heart rate information after a head collision that indicates whether or not the user is conscious. This information is useful to emergency responders as it enables them to judge the likely condition of the user who has experienced a collision event before they arrive on the scene.

In embodiments, the sensor module 1 comprises one or more of the following components: gyroscopes, 3-axis accelerometers 5, processors 2, wireless transmitters 12 and data storage buffers 21.

Figure 8:
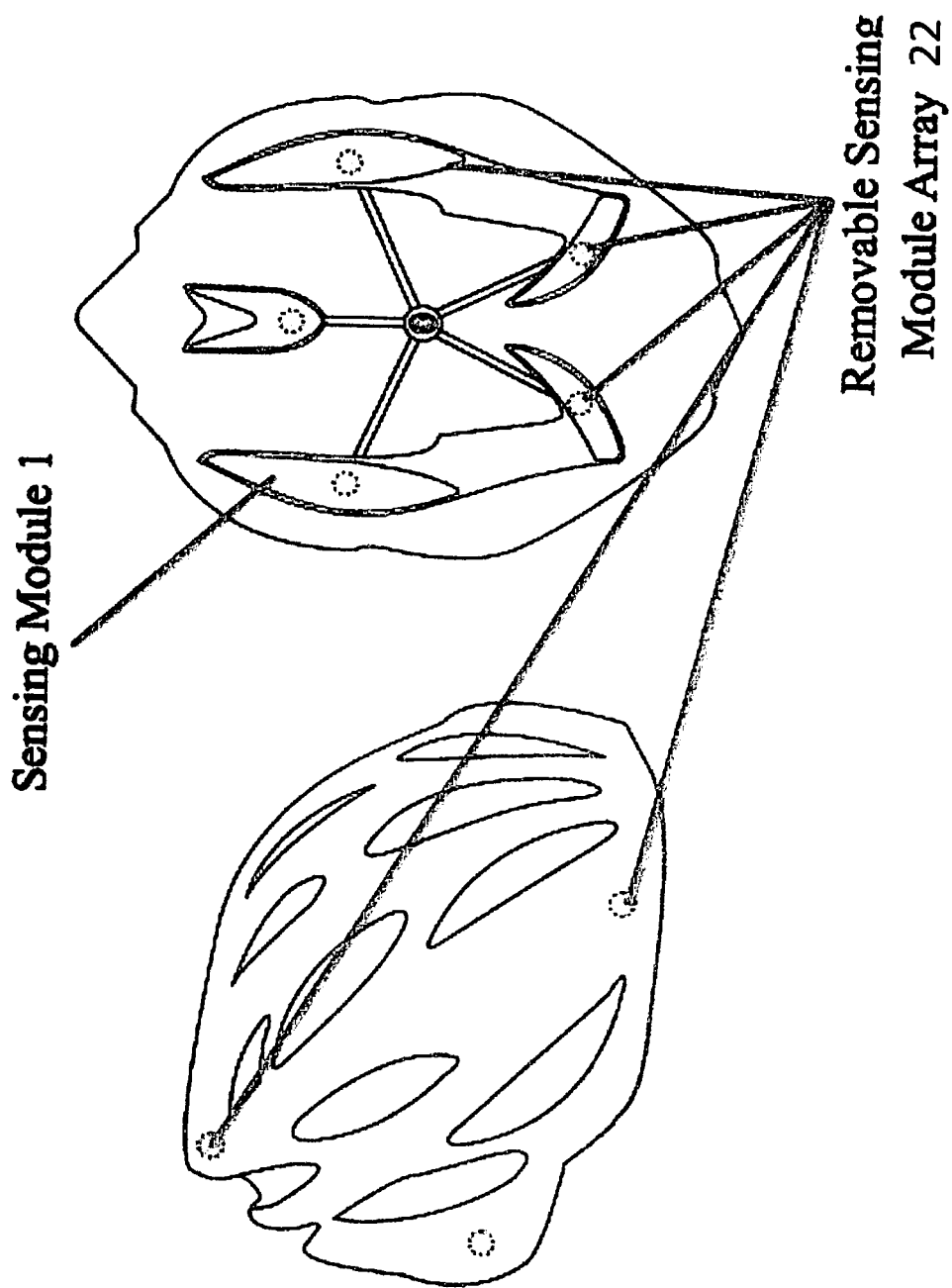
FIG. 8 illustrates placement of several sensor modules arranged in an array on a bicycle helmet.
Figure 9:
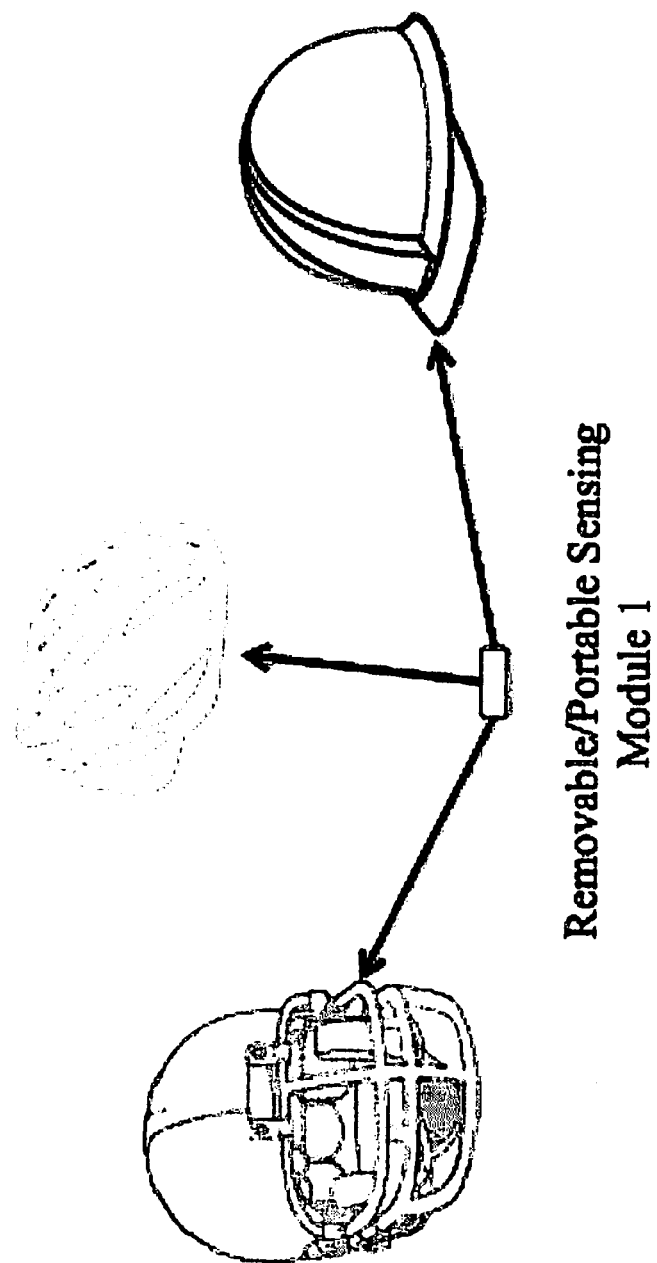
FIG. 9 illustrates several specialized helmet types among which the portable and replaceable sensor modules hereof can be switched.
Figure 10A:
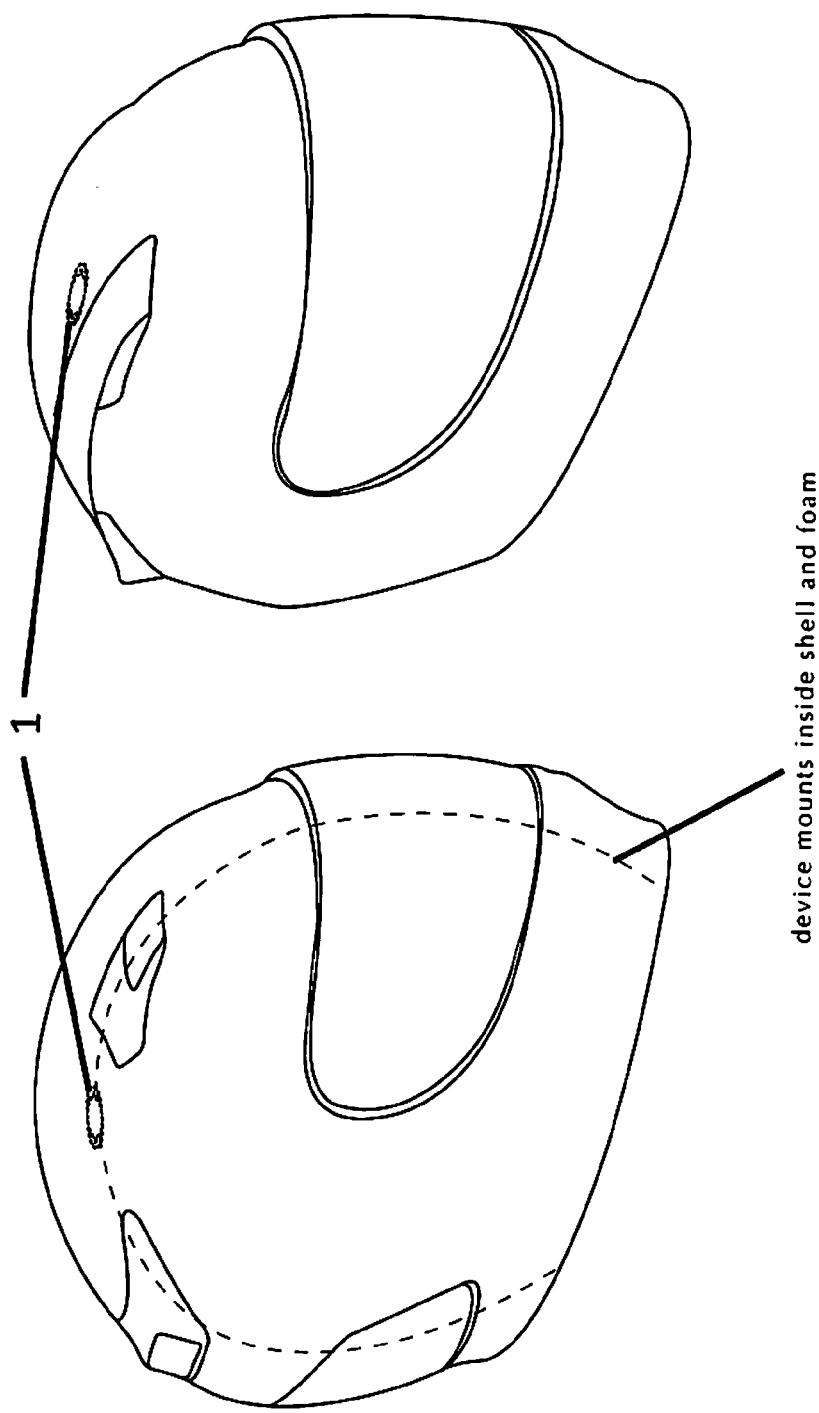
FIG. 10(a) is a motorcycle helmet configures with a sensor module.
Figure 10B:
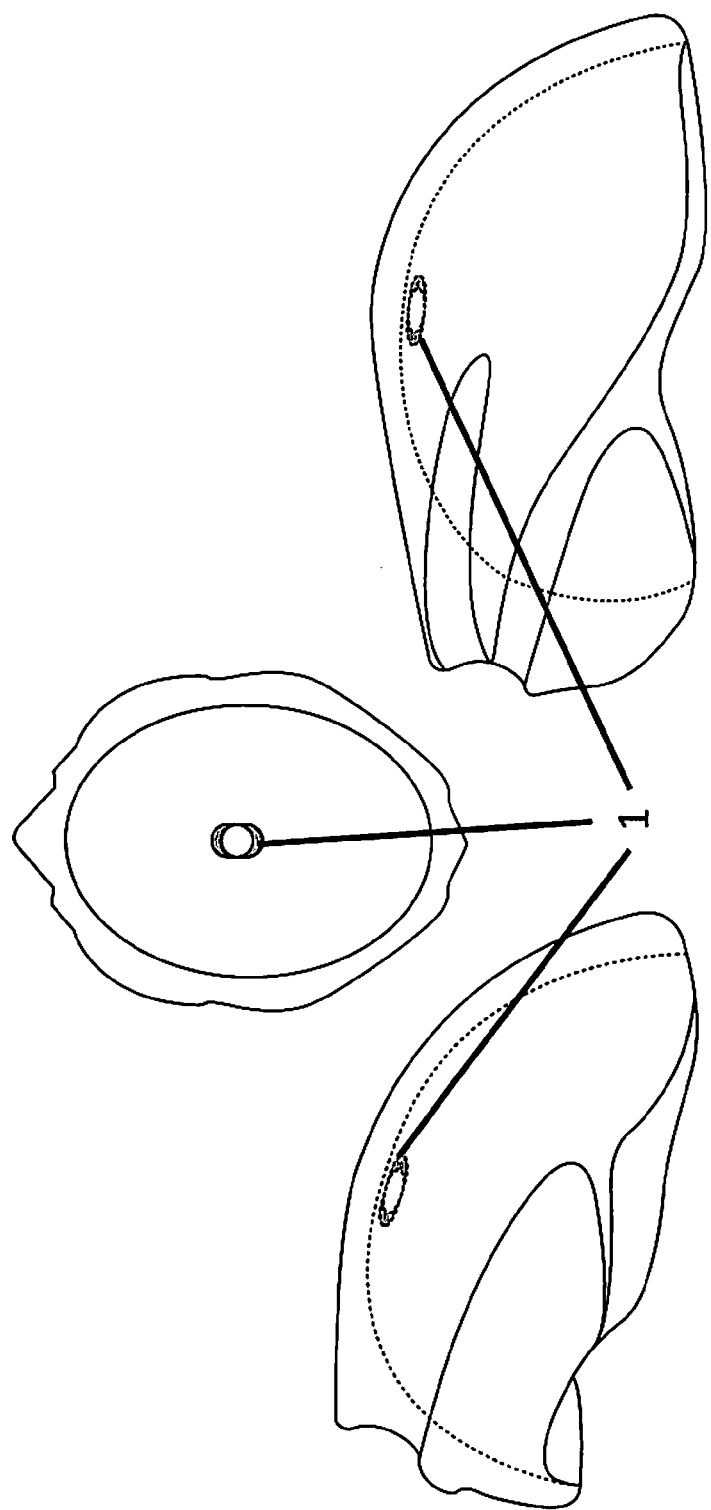
FIG. 10(b) is a bicycle helmet configured with a sensor module.
Figure 11A:
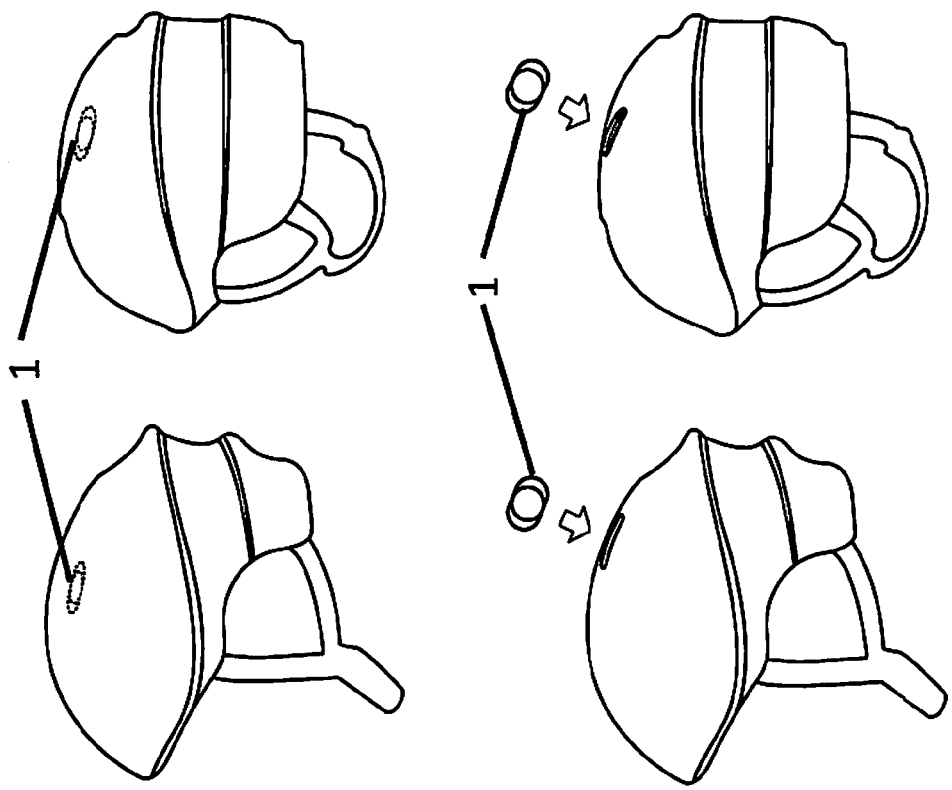
FIG. 11(a) illustrates a ski helmet configured with a module mounting means located at the top of the helmet.
Figure 11B:
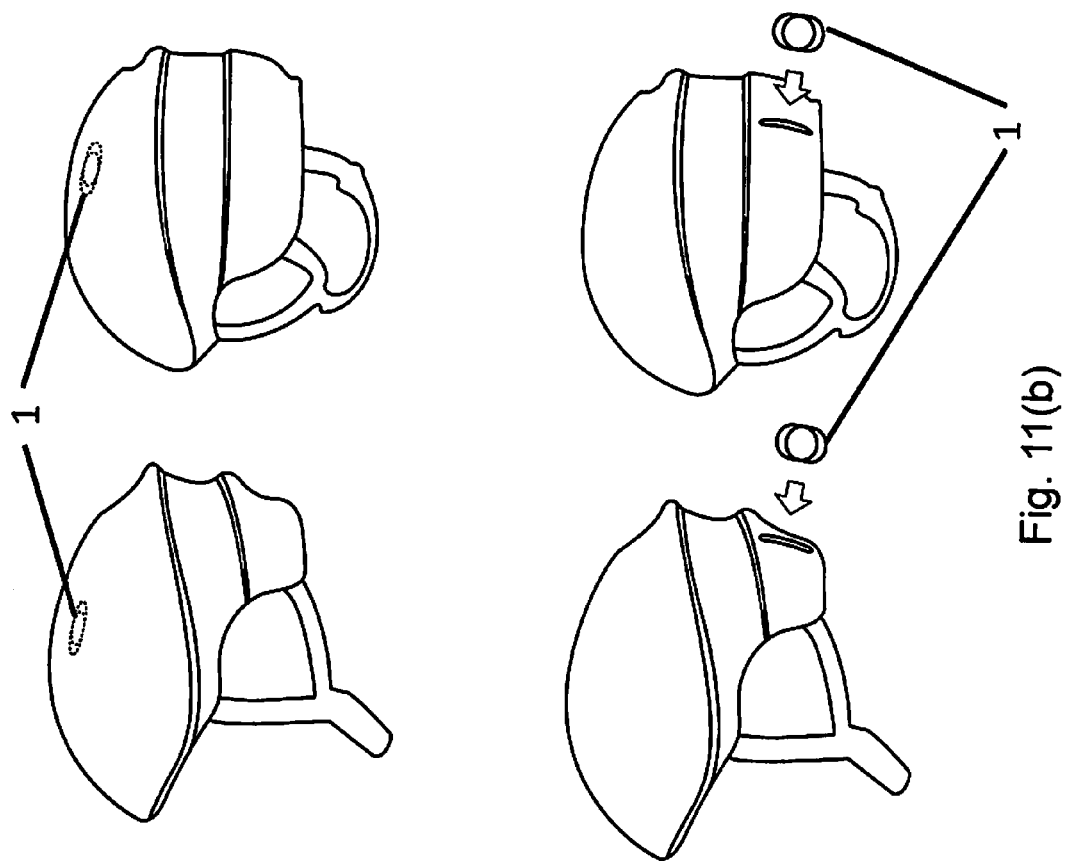
FIG. 11(b) illustrates a ski helmet configured with a module mounting means located at the side of the helmet.
Figure 11C:
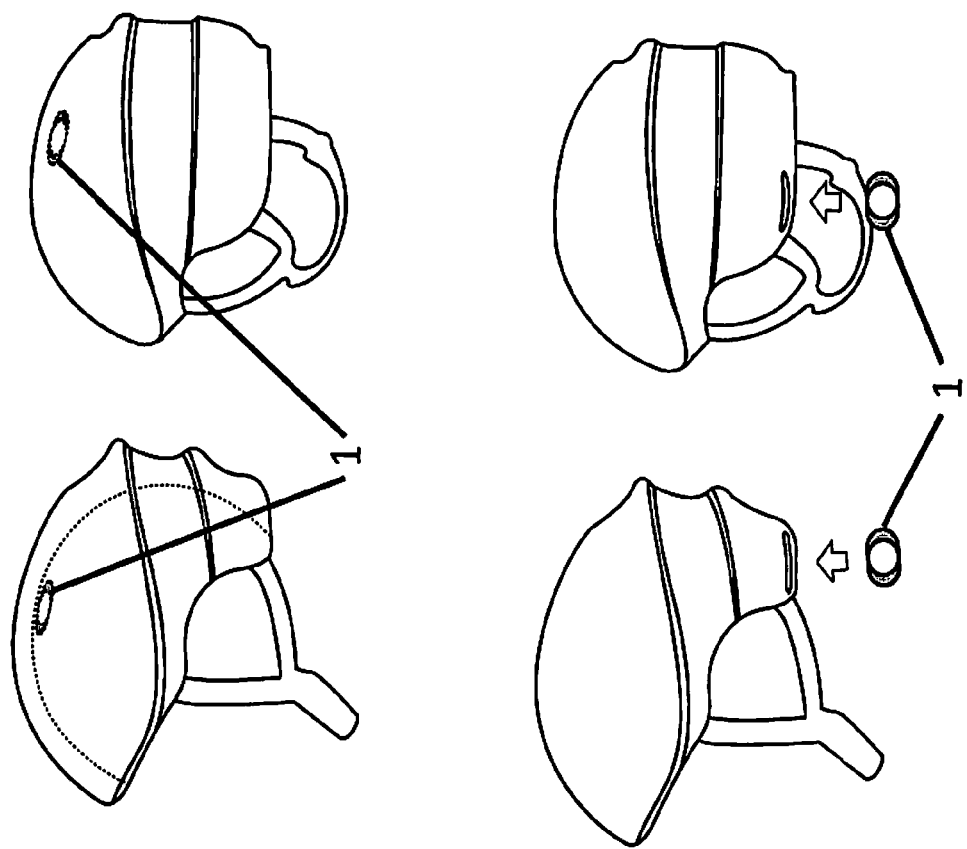
FIG. 11(c) illustrates a ski helmet configured with a module mounting means located at the bottom of the helmet.

One embodiment hereof features a removable sensor module or an array 22 of sensor modules FIG. 8, configured to be installed in different helmets FIG. 9, hats, head bands, other articles of clothing and other accessories configured so as to adequately receive them, such as via clips, pins, ties and other attachment devices, and the sensor module is configured, such as with similar or complementary attachment means, so as to allow the user to transfer the module among different accessories appropriate for intended activities FIGS. 10(*a*) and 10(*b*). A user is thus able to use the same sensor module for any number of activities and readily utilize different helmets or other accessories. In embodiments, the sensor module is removably attachable directly to a person or an object 6 FIG. 11(*a*)-11(*c*).

To measure the impact on a user in a collision 7 with another object, the impact-sensing device comprising a sensor module 1 is often mounted on the user's helmet FIG. 2. Force-sensing devices such as gyroscopes, accelerometers and or others known to the art can be integrated into a single unit removably attached to or removably placed within a helmet. In an embodiment, the helmet or the device is attached to a spring that keeps the sensor module in direct contact with the user's head.

The outputs of the force sensing devices are fed to a processor 2 that, together with processor clock time, integrates the acceleration and/or deceleration, expressed in terms of a multiple of gravitational acceleration (i.e. Gs), and calculates impact parameters such as jerk and jolt that can be recorded and transmitted to a remote receiving device and displayed to the user or stored for further processing and display. Sudden deceleration, which leads to jerk and jolt, is an important cause of DIA.

In embodiments, the impact sensing device 1 is directly in contact and encased in silicon or other layers of material with similar density of the average total brain (e.g. 1.05 g/mL) to approximate the effect of sensor being inside of the brain tissue.

In embodiments, the sensor module can measure directional linear collision forces and use a differentiator and integrator to calculate angular velocity, G-forces in 3 axes, angular jerk and/or angular jolt. Angular velocity and angular acceleration are used as a coordinate pair and compared against modeled data from literature sources to determine collision severity. Linear forces measured by an accelerometer can be used for overall translational (directional) force determination (which generally results in catastrophic injury), position of sensor and/or the user's head, and integrated head impact critera calculations (HIC) (see, e.g., Rowson, S. et al. (2009), "Linear and Angular Head Acceleration Measurements in Collegiate Football," J. Biochemical Engineering 131(6):061016, incorporated herein by reference to the extent not inconsistent herewith.

In embodiments, the sensor module also measures heart rate, brain waves, blood pressure, temperature and other biological parameters. In some aspects, the gyroscope and sensor are positioned relative to a person such that the axis of rotation of the gyroscope is vertical when the person is standing with his or her head normally aligned. In some embodiments the gyroscopes' axes are orthogonally positioned with respect to each other. The sensor module also comprises, in some embodiments, one or more devices for measuring and ensuring the integrity of the contact of the sensor with the person or object. These devices are positioned to determine impact forces, direction of a blow, contact of the sensor module with the head (i.e., whether or not the sensor module has become displaced from the user's head during impact). They can comprise one or more components selected from the group consisting of flex sensors, potentiometers, springs and or piezoelectric devices. Measuring angular velocity with a gyroscope is less complicated than measuring it with accelerometers. Angular velocity indicates what rotational forces are being exerted on the head when there is a collision event. Rotational acceleration and deceleration, as opposed to straight-on forces, cause the brain mass to rotate relative to itself and the skull and cause shearing forces, which result in disruption of axons and neuron communication and diffuse brain damage. This is a serious injury called diffuse axonal injury (DAI).

In some embodiments, the sensor module will not transmit normal movement of the user or object and can be dormant until it "wakes up" when appropriate movement is detected. While the gyroscope(s) and or accelerometer(s) continuously measure forces, the processor will 'ignore' signals below a threshold value. However, gyroscope and/or accelerometer units may be programmed to ignore signals below a selected threshold. Calculations and processing of these forces by the processor on the sensing unit will determine whether a significant impact has occurred. The sensor module can deliver burst data streams 23 instead of continuous data streams FIG. 12. A burst data stream is a short series of sequential data from the sensor that is processed for determination of collision event 7 property thresholds. The sensor module will transmit a burst of data 18 (e.g., a 30-second burst) when a selected low threshold has been detected. This allows the transmitter 12 of the sensor module to transmit intermittently, and not to be active 100% of the time, so that it acts primarily as a dormant receiver until it receives data for transmission. The transmission threshold can be quite low so as to allow processing of signals by the group tracking and communication device 3, or the software of a smart telephone 4, tablet, notebook, or other external communication device. In an embodiment, the analysis and interpretation of impact data (comparison thresholds) will be performed by the processor 2 on the sensor module and only signals that exceed the threshold will be transmitted to an external communication device for confirmation of impact and execution of notification steps.

In some embodiments, the sensor module processor comprises a signal-conditioning device 24 for conditioning and filtering signals FIG. 1. Digital filtering and preliminary calculations are done by the sensor module 1, and additional filtering can take place at the level of the group tracking and communication device 3 or other external device 4 such as a smart telephone, laptop, notebook, tablet, Bluetooth, or the internet 'cloud' 28 for cloud computing.

The power supply 25 of the system can be provided from a photovoltaic cell with a solar array carried or worn by the person being monitored, or by other means known in the art.

In embodiments, the signal processing 2 unit is operationally connected to an electronic storage 26 unit such as a flash or RAM memory device for receiving, storing and transmitting information.

In one aspect, the sensor module's processing unit converts raw analog signals from the gyroscope(s) and or accelerometer(s) to digital signals. It can also run a firmware 16 program that filters the raw data, does preliminary calculations, provides a time sequence, and sends the data to the wireless interface 12 for data transmission to an external device such as the group tracking and communication device, a smart telephone, tablet computer, notebook or Bluetooth module.

In an embodiment, the group tracking and communication device processor 15 is tasked with communication between the sensor module processor firmware 16 and the smart telephone application 17. It can also store data in its flash memory 18 and can have one or more of the following components: a GPS sensor 19, a Wi-Fi interface 20, and antennae for direct-to-Internet communication. Using software or firmware 27, the group tracking and communication device processor 15 compares the data from the sensor to threshold values to determine if a collision event occurred and sends the data to the smart telephone or other external device 4. The cellular telephone (smart telephone or tablet), or other external communication device is also programmed to handle all communication between the telephone or other external communicating device, the group tracking and communication device or sensor, and external systems to communicate and report back, and communicate confirmation of receipt of messages and other information provided by external systems.

Figure 12:
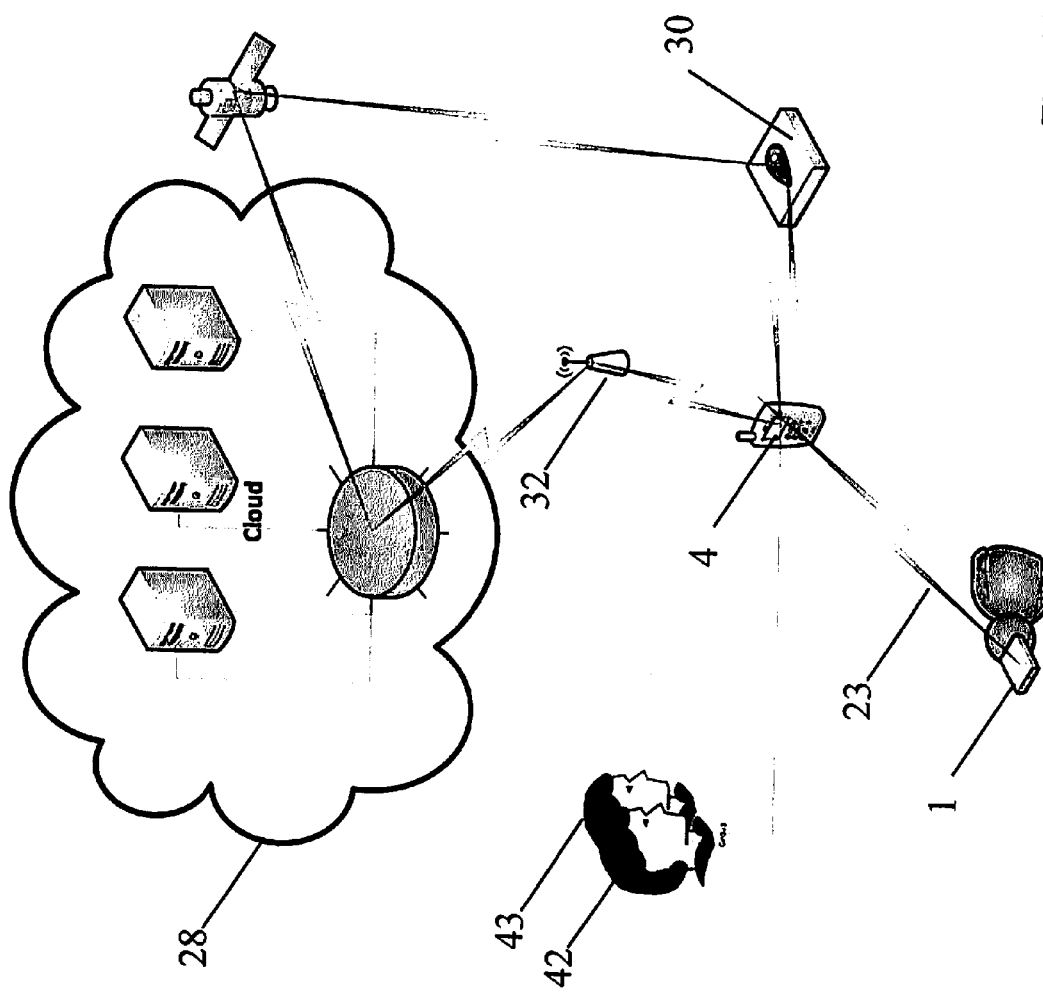
FIG. 12 illustrates signal flow among components of an embodiment of the sensing and reporting system hereof, including an internet "cloud" for storing and processing data.

In an embodiment, the electronic memory 18 component on the group tracking and communication device stores all collision data collected from the group of users connected to sensor modules connected to the group tracking and communication device, for upload into the internet 'cloud' 28 for cloud computing and return of information to the user and data repository FIG. 12. This allows the sensor module and group tracking and communication device to be used when there is no connectivity with other communication devices or the Internet, such that when cellular telephone or internet connectivity is restored, the collision impact data can be transferred for user or third party notification. For example, if the sensor in a child's helmet senses an impact collision above the threshold value, but the child does not carry a cellular telephone and there is no external communication device in range to receive the information FIG. 13(*a*), the information will be sent as soon as the external communication device comes in range FIG. 13(*b*).

In some embodiments, the group tracking and communication device is in signal communication with or comprises a mobile communication component, which is capable of receiving signals from multiple sensor modules of multiple persons or objects, and is capable of sending signals to multiple receivers.

In still another aspect, the group tracking and communication device is in signal communication with the internet "cloud" 28 for cloud computing which processes and accumulates demographic information, data on current and previous impact collisions, biological parameters and climatic data from multiple users, and data about the seriousness and type of previous impact collisions, and calculates correlations between the injury types and predicted severities and the other factors, and uses the correlations to predict the severity of a present impact collision event and reports the result back to the user or those responsible for monitoring. Users can enter follow-up results from medical attention to refine the rating of the predicted severity of future injuries and modify the threshold settings for reporting of collision events as necessary.

In an embodiment the sensor module senses the existence of adverse atmospheric conditions, such as the presence of bioweapons, dangerous gases such as carbon monoxide, and radon, and nerve agents. The sensor module, in some embodiments, can also measure oxygen levels and communicate when there is insufficient oxygen. Yet another embodiment also senses sonic, percussive and vibrational forces as might be experienced by the military or emergency responders. Devices and methods for sensing such conditions are known to the art and can be readily integrated into the above-described systems by those of ordinary skill in the art.

In some embodiments, the group tracking and communication device 4 is attached to or integral with a portable accessory such as a key fob 29, piece of jewelry, article of clothing, or other accessory designed to be worn, clipped on or carried about the person.

In some embodiments, the group tracking and communication device 3 is capable of transmitting and receiving signals to and from, and is operationally connected to, a Bluetooth or RF module 20, a position reporting unit 19, a cellular telephone 4, a global positioning system (GPS), a portable satellite communication device (SPOT) 30, a positioning satellite network 31, a cellular tower network 32, or an internet terminal FIG. 5.

In an embodiment hereof, the Bluetooth device operates with Bluetooth Low Energy technology which is converted to classic Bluetooth energy 33. Bluetooth Low Energy technology is capable of being powered by a small battery for a period of a year but is not capable of broadcasting signals over large distances, thus the Low Energy (LE) signal is converted for longer distance dissemination by another Bluetooth module using classic Bluetooth technology FIG. 5.

Figure 15A:
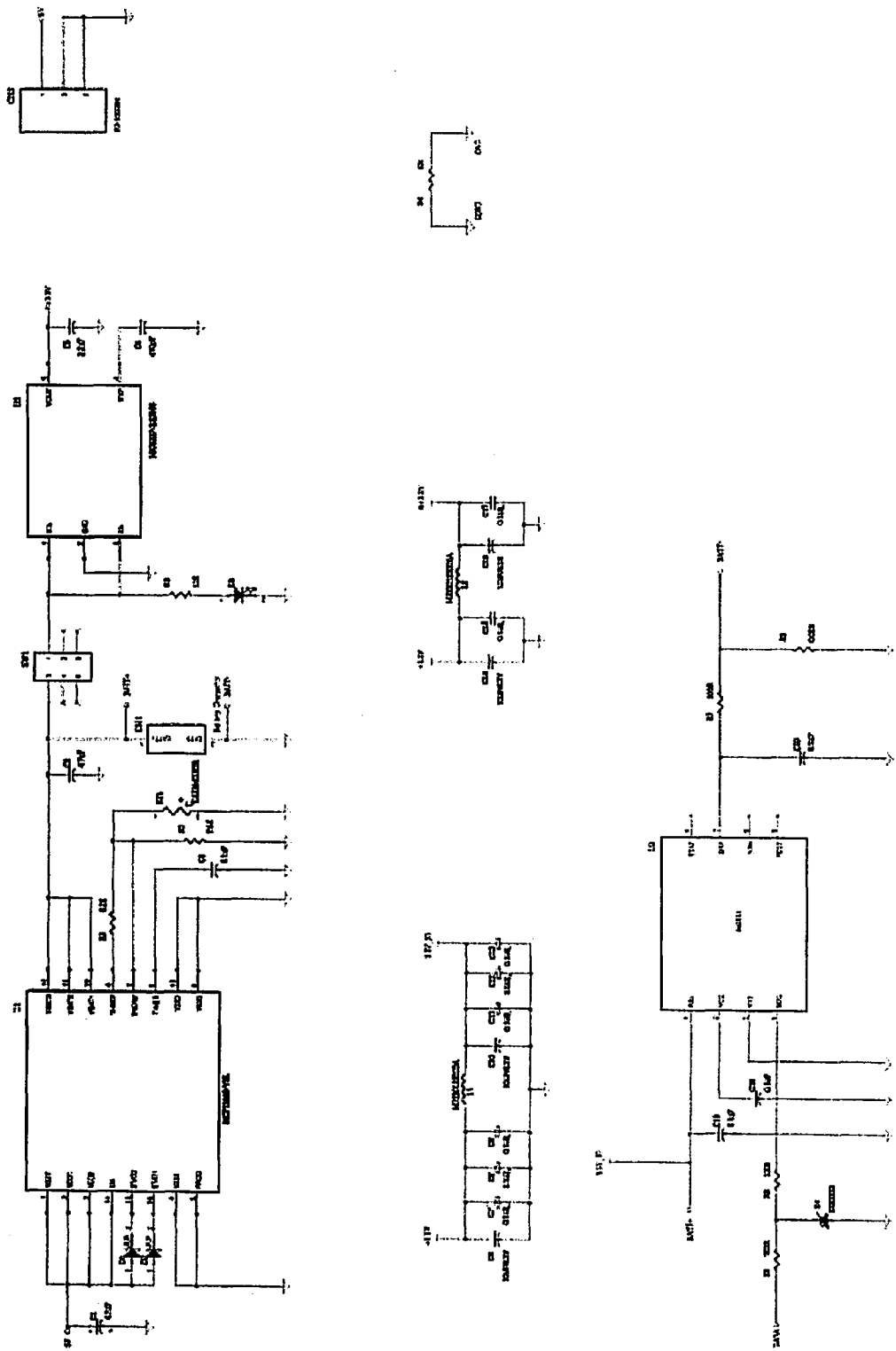
FIG. 15(a) is a schematic of integrated circuits for a battery charger and voltage regulator components of the BLEC.
Figure 15B:
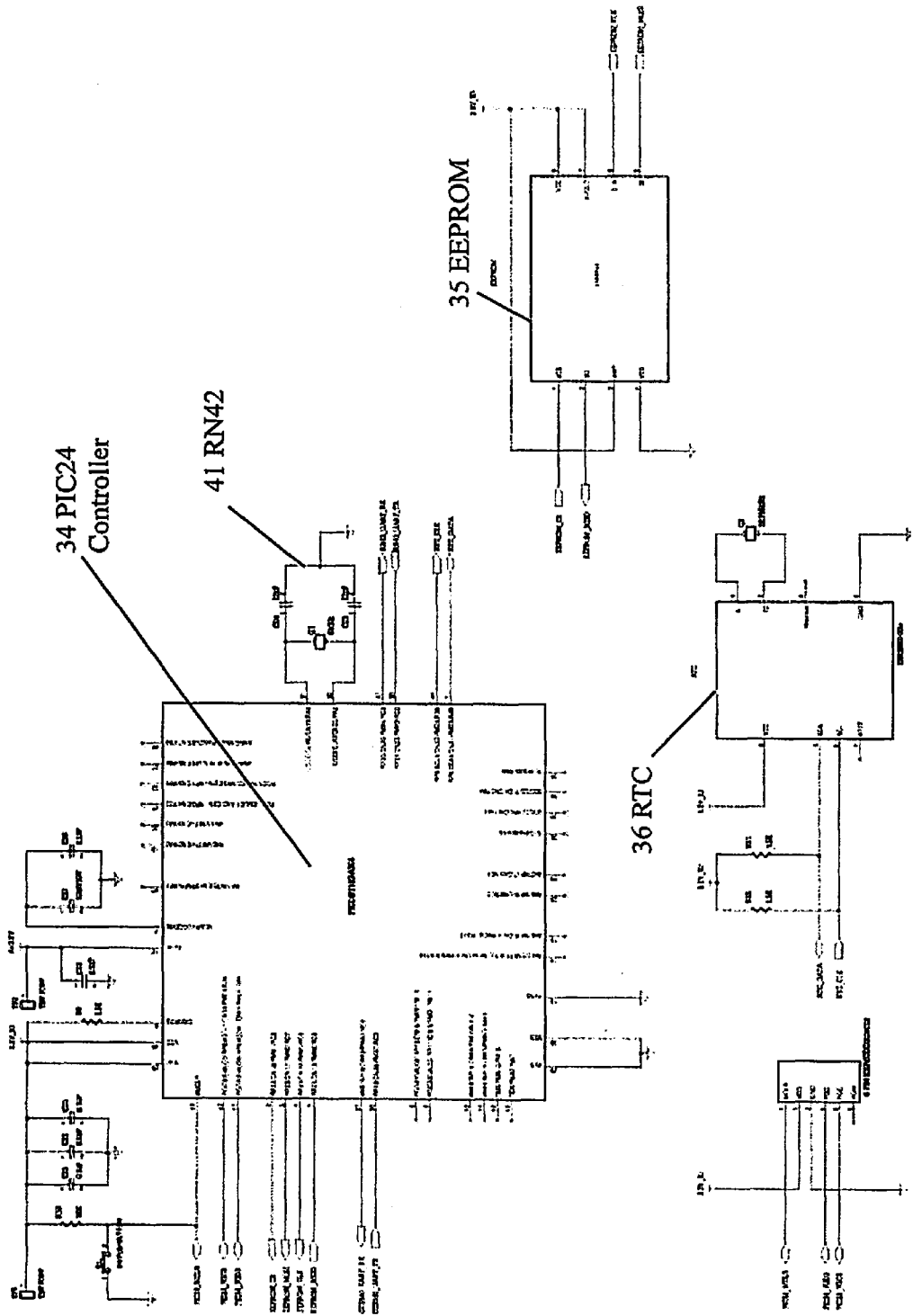
FIG. 15(b) is a schematic for Peripheral Interface Controller (PIC) and Real-Time Clock (RTC) electrically erasable programmable read-only memory (EEPROM) components for the BLEC.
Figure 15C:
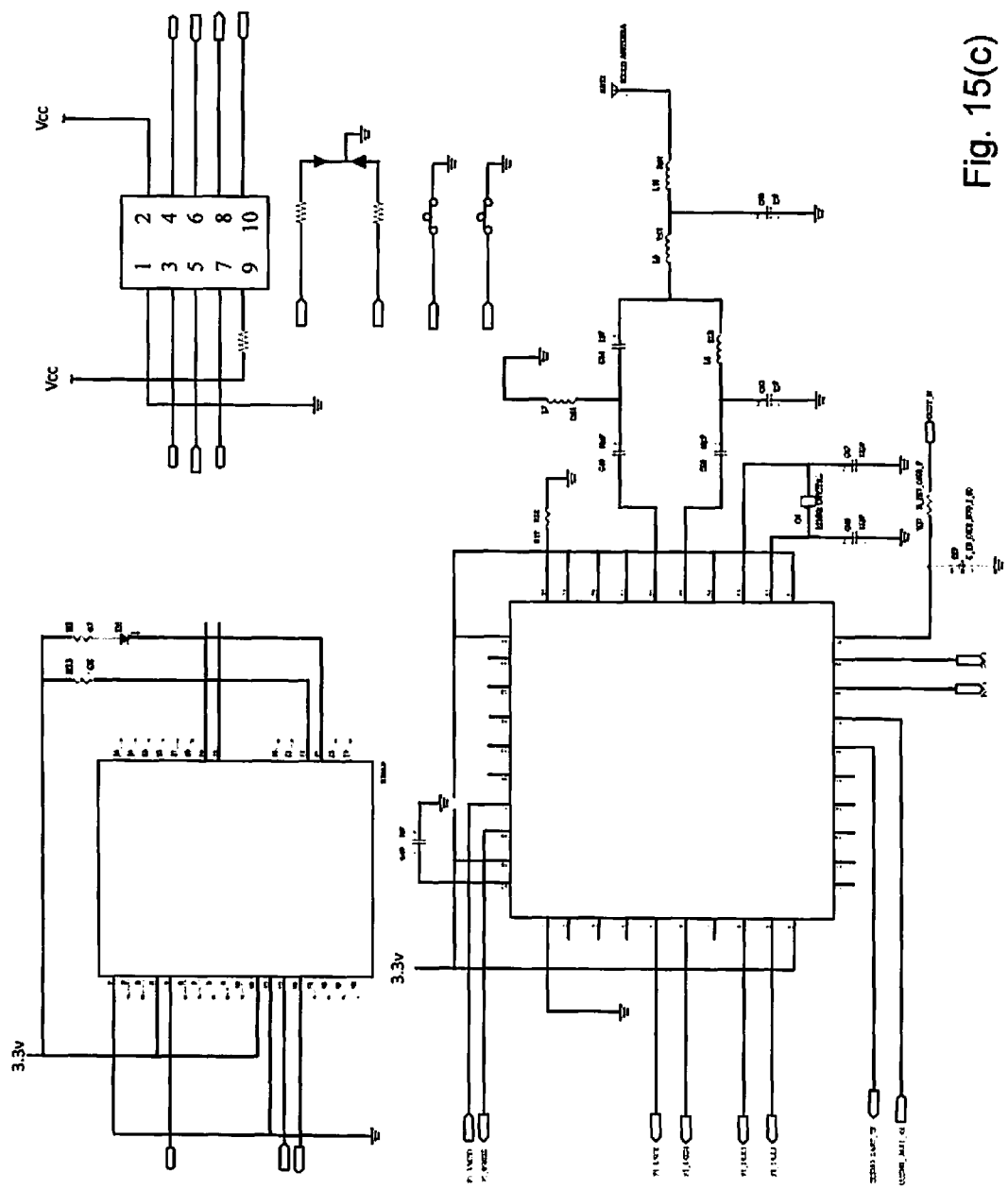
FIG. 15(c) is a schematic for a Bluetooth Low Energy Classic integrated circuit component of the BLEC.

In an embodiment hereof, the Bluetooth Low Energy (BLE) signal is converted to classic Bluetooth via a Bluetooth Low Energy to Classic converter (BLEC) FIG. 15(*a*). The BLEC is based on a PIC24 Controller 34 FIG. 15(*b*) which controls all the connected modules such as BLE, Classic Bluetooth module and related peripherals. The BLEC is configured for receiving data from other paired BLE modules and disseminating to the Group tracking and communication device, the Internet, the internet cloud for cloud computing, or other recipients. In an embodiment, firmware operates on the received data and if it meets threshold requirements it will save the data with a time stamp to Electrically Erasable Programmable Read-Only Memory (EEPROM) 35 in a pagewise format, such that the data can be read via wireless query made at a later point in time FIG. 15(*b*). If memory is limited in EEPROM, pre-existing data will be overwritten by predefined logic. The data is forwarded to the Classic Bluetooth module for transmittal to other classic paired Bluetooth modules or other recipients. In an embodiment an RTC module 1305 36 is used, connected to a PIC24 Controller via an SPI (Serial Peripheral Interface) interface. In an embodiment the EEPROM has 512K bits of memory. Since there are two controllers, a PIC24 controller 34 and a CC2540 (with 8051 core) 37, there will be two hex files to be downloaded to each. The hex file to the CC2540 is downloaded a single time and PIC controller downloads can vary depending on the application. The firmware hex file will be downloaded using respective connectors provided on the device. The BLEC draws power from a LiPo battery 38 and has a power regulator to regulate the power supply from the battery. This battery can be recharged with a power adapter FIG. 16(*a*). The BLEC has one reset switch, one power switch and five LEDs FIG. 16(*a*). The LED combinations are: blue LED for BLE module, Green LED for classic Bluetooth, and Green/Yellow/Red for battery status.

Figure 16A:
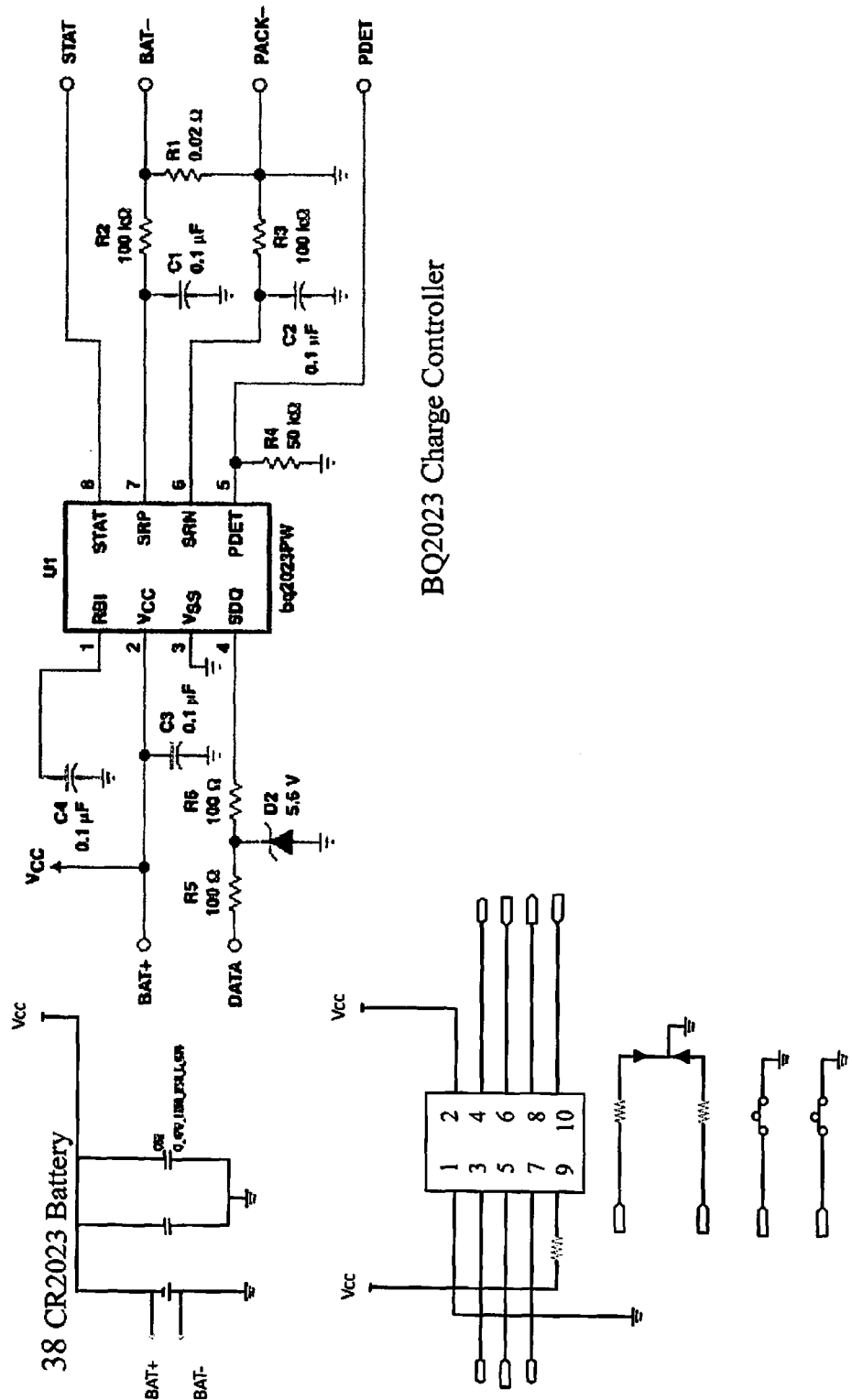
FIG. 16(a) is a schematic for integrated circuits for battery, battery monitor and LED switch components of the BEGA.
Figure 16B:
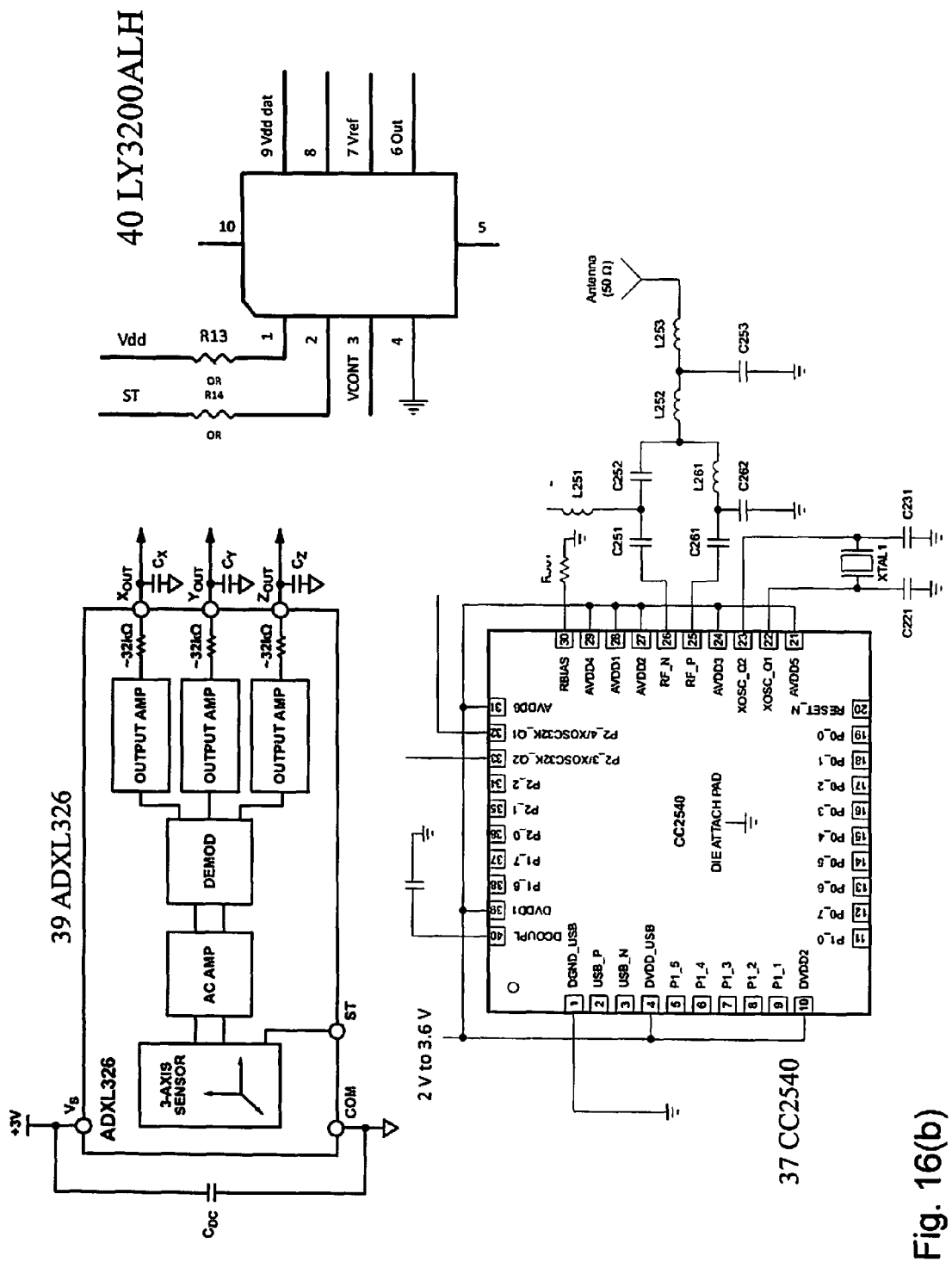
FIG. 16(b) is a schematic for integrated circuits for Bluetooth Enabled gyroscope and accelerometer components of the BEGA.

In an embodiment a sensor system consists of a BLE-enabled gyroscope with an accelerometer (BEGA) FIG. 16(*b*). This is a sensor system used to send the accelerometer and gyroscope data over the BLE network. It uses a 3 axis accelerometer, ADXL326 and a z-axis gyroscope LY3200ALH. Firmware is designed in such a way that it reads intermediate data and transmits it via BLE technology in a specified format and manner. The firmware is downloaded using the CC programmer from Texas Instruments. The BEGA has one Reset switch, a Power switch and one LED for power Indication. It also has a blue LED for Bluetooth module, and draws power from a CR2032 battery 38. In some embodiments the BEGA is equipped with WiFi or broadband technology and/or a GPS.

Another embodiment consists of a Bluetooth Enabled Acclerometer (BEA). A Bluetooth Enabled Accelerometer (BEA) uses a PIC24 Controller (Peripheral Interface Controller) 34 to integrate all the modules and uses the Bluetooth module RN-42 41. The RN-42 is used for short range, battery powered applications and is a Class 2 device with a range of only 15-20 meters and correspondingly low power consumption. The BEA uses an ADX326 accelerometer 39 to retrieve values from three axes. The BEA firmware reads and writes using a Micro SD card support. The firmware hex file is downloaded using the ICSP connector provided on the device, and uses a CR2032 battery 38 to supply power along with a regulator to regulate the power. The BEA has one power switch and one LED for power indication. The components in the BEA are designed to operate in the temperature range from about −40 to +85 C. In some embodiments, the BEA has further components consisting of a USB device support for data transfer from an SD Card, battery charging, Over the Air (OTA) enabled firmware and downloading support, SD card data transfer using a Bluetooth interface, LiPo battery charger support, and a Microsoft Foundation Class (MFC) application for firmware uploading via OTA and USB.

In some embodiments the group tracking and communication device sends demographic and collision data from collision events involving the same and other persons to an internet terminal which controls an internet-based server for storage 28 in a database and analysis by a prediction processor to predict the severity of injury from a measured collision event. The demographic data comprises information selected from the group consisting of size, weight, head size, age, sex, general health, medical history, activity being engaged in, income, health insurance, and other demographic data which is useful in determining the extent of the injury or the nature of the treatment to be recommended from medical personnel.

The likelihood of a serious injury significantly increases as a result of sustaining repeated impacts and injuries. In some embodiments the database also contains data representing the type and severity of injuries sustained by a persons having specific demographic characteristics as a result of different types of collision events—allowing for a comparison of demographic characteristics similar to those of a current module user and the type of collision event and impact sustained to predict the severity of injury of a current collision event. An internet-based server 28 comprises or is operationally connected with a prediction processor programmed to analyze the collected data in the database and correlate properties of angular velocity over time, demographic characteristics of users, and type and severity of injuries sustained from collision events, to compare the data from a user experiencing a current collision event with previously-collected data, and to generate signals which predict the severity and type of injury to the user that has resulted from the current collision event.

In some embodiments, the prediction processor comprises software or firmware to determine if a collision event of sufficient magnitude for reporting to the user or a remote location has occurred, a broadband or low frequency wireless interface; and/or an antennae for direct-to-Internet communication. The prediction processor performs functions including: receiving and storing data in a flash memory and/or determining global position via a GPS. In some embodiments, the receivers of said processor are those of Internet connection devices and portable communication devices such as cellular telephones, e.g., cellular telephones connected to communication satellites 49.

In an embodiment, the portable communication device is programmed to send messages through devices selected from the group consisting of cellular telephone towers, communication satellites, such as those accessed via a SPOT device 30, to recipients selected from the group consisting of third party emergency contact resources 42, rescue/emergency provider network 9, and user-defined contacts 43.

The sensor module is generally enclosed by an appropriate housing, preferably consisting of a brain-similar density material (e.g. formulated soft silicone) and an exterior housing, such as a plastic injected molded housing known in the art. The interior encasement is material similar to the average total brain density (e.g. 1.05 g/mL). The exterior encasement is rugged to withstand the exposure to elements such as snow, water and dirt. A water-tight access port permits for the removal and replacement of the battery within the housing as required, and as known in the art. The housing can also include a window in order to see the display. Access can be provided through pliant rubber coverings, or the buttons and/or switches can be made in the form of keypads, as known in the art, that integrate directly with the surface of the housing. Other housing and input means are known to the art. In each case the buttons and/or switches and housing cooperate so as to provide an environmentally secure enclosure for the electronics such as the group tracking and communication device, the sensor module and the sensor module processor while providing an operable user interface.

The housing can include a universal interface which provides flexible and conformal mounting to a variety of surfaces, such as to the relatively flat surface of a snowboard or to a round bar on a mountain bike. The universal interface is designed to permit standalone units to be sold in stores regardless of how or where a user mounts the unit.

The housing can be color coded (e.g., for child and large and small adult users), and/or can be equipped with personalizable labels or other markings to enable users to easily identify their own sensing modules among others belonging to members of a family, team, or other group.

In some embodiments, the sensor module sends a signal encoding a message selected from the group consisting of: (1) a message to the person connected to the sensor that he has been involved in a minor collision event which has been stored in his sensor device, and advising of the accumulated collision events he has experienced, and making a recommendation as to whether or not he should seek medical attention; (2) a message to the person connected to the sensor that he has been involved in a moderate collision event and advising that and recommending that he see a doctor; (3) a message to a third party emergency contact resource that the person has been involved in a collision event of a specified severity and a message to the person advising that the emergency contact resource has been notified; (4) a message to a rescue/emergency provider network that the person has been involved in a collision event requiring emergency response and a message to the person that the rescue/emergency provider network has been notified; and (5) a message to the group tracking and communication device of a monitor that a person has involved in a collision event and making a recommendation as to whether or not the person should receive medical attention. Said messages can be of many types, including SMS text messages, voice messages, internet protocol data exchanges, and alarms.

In an embodiment, the sensor module comprises a power source such as a battery or a capacitor, which can be either charged or replaced by the user. In an embodiment the power source can be charged from a photovoltaic cell-lined outer-helmet layer on so-equipped helmets, a charging pad or a contact charger.

The sensor module further comprises a sensing element, such as one or more gyroscopes, and a three-axis accelerometer configured to detect linear accelerations of the helmet. The sensing element can comprise any one or more components selected from the group consisting of: MEMS (microelectric mechanical systems), piezoelectric accelerometers, force or strain gauges, force or strain transducers, and force-sensing textiles. Additional sensing elements known to the art can be added to the sensor module. Additionally the sensor module comprises a signal processor 47 or a multiplicity of signal processors interfaced with the sensing elements of the sensor module.

Generally, the signal processor is configured for a plurality of functions including filtering low frequency signals and analog-to-digital or digital-to-analog signal conversion. The sensor module can further comprise a central processing unit 44, data memory buffer 21, data logger 45, and removable flash memory unit 26, and is configured to receive, process, and record both signals and processed data from the sensing element 5. The sensor module can additionally comprise a RF transmitter 19 communicatively interfaced with a processing unit 2, a data memory buffer 21, data logger 45, and removable flash memory 26 unit to allow for transmission of collected impact data to a receiving device FIG. 1(a).

The sensor module can further comprise a RF receiver 46 to allow receipt of confirmation from a remote receiving device of data transmission to said receiving device. Additionally, the RF 19 transmitter allows for receipt of a data transmission request and/or prompt to or from the sensor module so that the user can access impact or other data via a receiving device without having sustained an impact in excess of a transmission-triggering intensity.

The sensor module and/or group tracking and communication device are configured with software or firmware 16 with processing logic to utilize an RF transmitter 12 to (1) transmit data relating to any impact in excess of a preset transmission-triggering intensity; (2) utilize an RF receiver 46 to confirm the receipt of said transmission by a receiving device 4 or periodically resend the data either until confirmation is received or for a preset period of time; and (3) if there is no confirmation within the preset period of time, to re-encode the transmission of the impact for an immediate alert to emergency responders 9 or other end users and attempt a transmission to any receiving device in the vicinity of the sensor module capable of relaying the signal; and (4) to utilize the RF receiver 46 to accept prompts to transmit any impact data stored within the sensor module or group tracking and communication device via the RF transmitter 12 and make said data available for analysis.

The receiving device is configured to receive transmissions in the frequency range of the RF transmitter, and is configured with software or firmware with processing logic configured to receive and store collected impact data and employ any of the receiving device user interface functionalities including audible, visual, or tactile signals that can be perceived by a user.

The receiving device is further configured with software or firmware and processing logic to require user input to acknowledge the receipt of an alert; and is configured with software 17 and processing logic to alert emergency responders and summon assistance if the user 6 or a monitor 13 fails to acknowledge the receipt of the alert.

The receiving device is further configured with software and processing logic to allow the user to review of stored impact data utilizing the user interface functionalities, and designate any of the data for transmission or download to a remote computer or network storage device.

In an embodiment the sensor module 1 is removably attached to a bicycle helmet.

The sensing elements of the sensor module (e.g., a three-axis accelerometer and/or one or more gyroscopes) are configured to sample acceleration and deceleration rates at a frequency of up to 100,000 Hz. In an embodiment, the control logic of the sensor module can be configured so sample rates can be varied and reduced upon prolonged absence of acceleration/deceleration (when the sensor module is at rest) or increased when any accelerations are detected—a power-saving feature.

Subsequently, sampled accelerations are filtered, processed, and rotational velocity and accelerations and/or decelerations exceeding 5.5 rad/s or 1230 rads/s$^2$ are recorded and stored in a removable flash memory unit. In an embodiment, the recorded accelerations and/or decelerations are made available for further analysis by the processing logic and if the processing logic detects a triggering acceleration or deceleration in excess of 22.3 rad/s or 5022 rads/s$^2$ (or a % of these values as described above), a data transmittal to a receiving device via the RF transmitter is triggered.

In an embodiment, as sampled accelerations are filtered and processed, a detection of a triggering acceleration or deceleration prompts a data transmittal to a receiving device via the RF transmitter, and the triggering acceleration or deceleration is subsequently recorded and stored in the removable flash memory unit. This embodiment assures that the triggering acceleration or deceleration is still reported even if the removable flash memory unit 26 fails.

In an embodiment, the sensor module or group tracking and communication device is configured so that the recorded data is encrypted prior to any transmittal to the user's communication device, effectively pairing the user's sensor module 1 with the user's communication device 4, preserving the privacy of the user's data.

In an embodiment, the sensor module 1 is further communicatively configured with the user's communication device 4 via an RF or other transmitter 12 and an RF or other receiver 46, so that that the user's communication device confirms the receipt of a data transmittal from the sensor module.

In an embodiment, the sensor module and/or the group tracking and communication device and the user's communication device are configured such that the user's communication device confirms to the sensor module or group tracking and communication device the user's acknowledgment of a data transmission. The sensor module or group tracking and communication device is configured to (1) periodically repeat data transmissions till the confirmation of receipt and/or user acknowledgment is received, or (2) upon the expiration of a preset maximum alert time or transmittal attempts or predetermined time for user acknowledgment, the sensor module or group tracking and communication device is configured to attempt transmitting un-encrypted version of the data to any other (secondary) receiving device equipped with software and processing logic to receive data signals emitted from the sensor module or group tracking and communication device, where such secondary receiving devices both alert their users of the occurrence of a collision event other adverse conditions and automatically pass an alert to emergency responders, effectively commandeering the secondary receiving device to transmit an emergency alarm to the emergency responders.

When the user's communication device receives a transmittal of a triggering acceleration signal, it is configured to alert the user via all communication device interface functionalities, sounding an audible alarm, flashing a screen and/or other light sources integral to the receiving device, and/or vibrating receiving devices equipped with tactile alert functionalities. The user is prompted to acknowledge the alarm and presented with the measured value of the triggering force or an interpretation of this force in terms of predicted severity of injury and/or recommended action. In an embodiment, user failure to acknowledge the alarm within a predetermined period triggers the user's communication device to communicate the alarm to an emergency response service, transmitting the triggering acceleration data and user information such as user name, medical history information, and any other information available to the user's communication device separately from the sensor module, such as information that relates to the geographic location of the receiving device and which can aid in locating the user.

In an embodiment, the sensor module is configured to alert multiple receiving devices and to periodically repeat transmissions of triggering acceleration data until all receiving devices confirm receipt of the transmission. In such an embodiment, a child is equipped with the sensor module and for example, both the parents and secondary persons-in-charge (teachers, coaches, child-care staff) are alerted of a triggering impact or other adverse condition.

In an embodiment, a multiplicity of sensor modules are configured on multiple wearers and all the modules are configured to report to one or more receiving devices FIG. 7. For example, a parent or a coach 13 can monitor sensor modules of several children or athletes 6. In an embodiment, the system is configured for military applications where the sensor module is removably fixed to a soldier's helmet or uniform, and where the sensor module further comprises sensors for biometric, climatic, atmospheric, explosive and other battlefield data allowing for battlefield alerts of impacts due to falls, explosions, bioweapons the presence of harmful gases such as carbon monoxide, radon, oxygen depleted-atmospheres. This embodiment allows for real time battlefield-command reporting of impacts sustained by soldiers and it allows for more efficient deployment of medical assistance, deployment of reinforcements, and general monitoring of soldiers' health. In an embodiment, the triggering acceleration, triggering temperature, triggering heart rate, triggering pressure and/or other triggering data are reported to the soldier equipped with a secure communications device and that data is further reported up to the soldier's immediate superior, allowing for battlefield monitoring of individual soldiers.

The foregoing embodiments are also useful for use by emergency first responders such as fire crews and others required to work in dangerous environments.

In an embodiment, the sensor module and/or the group tracking and communication device and the user's communication device are configured to comprise control logic and software to utilize a control module RF or other transmitter 12 to periodically transmit a data transfer prompt to a designated receiving device 4 and to utilize the designated receiver to receive said prompt and use control logic to determine if the prompt originated from a designated sensor module, and upon making this determination, to utilize the designated receiving device's RF or other transmitter to command the sensor module via the sensor module receiver to commence data transfer to the designated receiving device.

In an embodiment, the sensor module is configured to receive a data transmission prompt via its RF or other receiver 46. Such prompt is transmitted from a communication device 4 paired with the sensor module's receiving device, and conveys predetermined user confirmation and authorization for the sensor module to transmit collision event data stored on its removable storage memory 26 to the prompting receiving device. The sensor module can be configured to periodically transmit collision impact data stored on its removable storage memory 26 in the absence of a triggering collision event, and to make such data available for further analysis and viewing by the user.

What is claimed is:

1. A system for sensing, analyzing, and reporting one or more collision events of a person or object with another person, or object, said system comprising:
   a sensor module consisting of at least one sensor configured to be operationally connected to one or more persons or objects and capable of sensing angular velocity of said person or object as a result of said collision events over time and of producing first signals comprising information representing properties of said angular velocity over time;
   a sensor module processor in signal communication with said sensor module and programmed to analyze said information and compare it to one or more threshold values indicative of a severity of said collision events; and
   a transmitter in communication with an output of the sensor module processor to produce a second signal comprising data representing the results of said comparison(s) for transmission to a separate communication device programmed to provide a notification of a severe collision in response to the second signal.

2. The system of claim 1 wherein said sensor module comprises one or more elements selected from the group consisting of: gyroscopes, 3-axis accelerometers, MEMS (microelectric mechanical systems), piezoelectric accelerometers, force or strain gauges or transducers, and force-sensing textiles.

3. The system of claim 1 also comprising components capable of analyzing and reporting information selected from the group consisting of consisting of climatic data, biometric parameter data, the presence or levels of nerve agents, poisonous gases, bioweapons, oxygen, and sonic, percussive and/or concussive results of explosions.

4. The system of claim 1 also comprising a user interface capable of producing a perceptible audible, visible, or tactile stimulus to the user in response to a signal received by a receiver at said user interface.

5. The system of claim 1 wherein said sensor module processor is equipped with a low energy communication component for receipt and transmittal of signals.

6. The system of claim 1 where the low energy communication component is Bluetooth Low Energy (BLE) component.

7. The system of claim 1 wherein the low energy communication component also comprises a converter for converting the BLE signal to a classic Bluetooth signal for further transmission.

8. The system of claim 1, wherein said sensor module measures angular velocity, and/or G-forces in three axes and calculates at least one of angular acceleration, angular deceleration, jerk, and jolt.

9. The system of claim 1 wherein the sensor module is removably attachable to said person or an item of said person's clothing, equipment or accessories.

10. The system of claim 1 comprising an encryption component for encrypting signals prior to transmission.

11. The system of claim 1 further comprising a group tracking and communication device with a second receiver for receipt of said second signals and which is attached to one or more people or objects and is programmed to send third signals to one or more receivers.

12. The system of claim 1 wherein said sensor module comprises at least one gyroscope and said sensor module is positioned relative to said person such that the axis of rotation of said gyroscope is vertical when the person is standing with his or her head normally aligned.

13. The system of claim 1 wherein the sensor module comprises sensors for measuring one or more biological parameters selected from the group consisting of: heart rate, brain waves, blood pressure, and temperature.

14. The system of claim 1 wherein said sensor module comprises two or three gyroscopes with axes orthogonally positioned with respect to each other.

15. The system of claim 1 wherein said sensor module is insensitive to velocities resulting from normal movement of said object or person.

16. The system of claim 1 wherein said sensor module also comprises a component capable of detecting directional linear collision forces.

17. The system of claim 1 wherein said sensor also comprises a component capable of detecting the integrity of contact between the sensor module and the person or object to which it is attached.

18. The system of claim 1 wherein said sensor module is positioned adjacent to or atop said person's head for detecting angular velocity of the head during normal movement and head collision.

19. The system of claim 1 wherein said sensor module is positioned adjacent to a spring positioned at the inside top of a helmet, such that in use said spring pushes said sensor module against the head of a wearer of said helmet.

20. The system of claim 1 wherein said sensor module is housed directly within a material with approximate density similar to brain density in the range of 0.95 g/mL to 1.15 g/mL.

21. The system of claim 1 wherein said sensor module is attached to or integral with an accessory carried or worn by said person.

22. The system of claim 11 wherein said group tracking and communication device is attached to or integral with an object designed to be easily carried about or attached to a person.

23. The system of claim 1 wherein said sensor module is removably attached to the person or an accessory worn or carried by a person and is capable of being removably attached to another person or accessory.

24. The system of claim 1 wherein said sensor processing unit comprises a signal-conditioning device for filtering and conditioning signals from sensor.

25. The system of claim 1 wherein said signal-conditioning device filters low frequency signals and converts them from analog to digital or digital to analog.

26. The system of claim 1 wherein said signal-conditioning device comprises a band pass filter to allow selected signals to be transmitted.

27. The system of claim 1 wherein said sensor processor comprises a differentiator for determining a plurality of time derivatives of accumulated angular velocity signals from a gyroscope over a predetermined period of time.

28. The system of claim 1 wherein said time derivatives are selected from the group consisting of angular acceleration, angular jerk, and angular jolt.

29. The system of claim 1 further comprising an integrator for integrating said time derivatives over a predetermined period of time.

30. The system of claim 1 also comprising a power supply connected to said sensor module.

31. The system of claim 1 wherein said power supply is selected from the group consisting of photovoltaic cells, charging pads, contact charger adaptors and converters.

32. The system of claim 1 wherein said sensor module comprises a wake-up module that begins functioning when movement is detected.

33. The system of claim 1 wherein said sensor module produces a burst data stream.

34. The system of claim 1 also comprising an electronic storage unit operationally connected to said sensor module processor, said electronic storage unit being capable of receiving, storing and transmitting information from said first and second signals to and from said sensor module processor.

35. The system of claim 1 wherein said electronic storage unit comprises a flash or RAM memory device or a micro SD card.

36. The system of claim 1 wherein said first receiver comprises a component selected from the group consisting of portable communication devices, processors, and internet terminals.

37. The system of claim 1 wherein said processor is selected from the group consisting of notebook computers, tablet computers, and personal digital assistants.

38. The system of claim 11 wherein said group tracking and communication device comprises or is operationally connected to a position reporting unit capable of generating a signal representing the location of said device and/or said sensor module.

39. The system of claim 11 wherein said group tracking and communication device comprises an interface for direct connection to the Internet.

40. The system of claim 11 wherein said group tracking and communication device is a cellular telephone.

41. The system of claim 1 wherein said cellular telephone comprises a global positioning system.

42. The system of claim 1 wherein said cellular telephone is in operational connection with a positioning satellite network.

43. The system of claim 1 wherein said cellular telephone is in operational connection with a portable satellite communication device (SPOT).

44. The system of claim 1 wherein said SPOT is capable of sending signals to a communication satellite.

45. The system of claim 11 wherein said group tracking and communication device is capable of sending to and receiving signals from a portable satellite communication device.

46. The system of claim 11 wherein said group tracking and communication device is capable of sending signals to and receiving signals from a cellular tower network, an internet terminal, or a receiving component of an internet cloud.

47. The system of claim 1 wherein said second signals comprise demographic information about the person connected to sensor module and information about properties of a collision event and/or another adverse condition.

48. The system of claim 1 comprising an internet-connected server capable of receiving said second signals and comprising information collected from other collision events and/or adverse situations involving the same and other persons.

49. The system of claim 1 wherein said demographic information comprises information selected from the group consisting of size, weight, head size, age, height, sex, income, political affiliation, net worth, race, ethnicity and lifestyle habits.

50. The system of claim 1 wherein said database also comprises stored information representing the type and severity of injuries sustained by persons as a result of experiencing previous collision events, and information representing properties of angular velocities over time during each said previous collision event.

51. The system of claim 50 wherein said internet-connected server comprises or is operationally connected with a prediction processor programmed to analyze data in said database and correlate properties of measured angular velocity over time with type and severity of injuries, and to generate prediction signals which predict the severity and type of injury that results from a subsequent collision event.

52. The system of claim 51 wherein said prediction processor comprises components capable of performing one or more functions selected from the group consisting of: receiving and storing data in a flash memory; determining global position via a GPS; and generating and transmitting signals.

53. The system of claim 52 wherein said prediction processor comprises one or more components selected from the group consisting of: broadband or low frequency wireless interfaces; antennae for direct-to-Internet communication; and software to determine if a collision event having measured properties exceeding said threshold values has occurred.

54. The system of claim 11 wherein said group tracking and communication device is attached to or integral with a device designed to be worn, clipped to, or carried upon the person.

55. The system of claim 11 wherein said group tracking and communication device is in signal communication with one or more mobile communication devices comprising receivers capable of receiving signals from multiple sensor modules operationally connected to multiple persons or objects, and is capable of sending signals to multiple receivers.

56. The system of claim 55 wherein said receivers of said mobile communication devices are selected from the group consisting of: Internet connection devices; portable communication devices, and communication satellites.

57. The system of claim 55 wherein said mobile communication devices are cellular telephones.

58. The system of claim 55 wherein said mobile communication devices are programmed to send messages to entities selected from the group consisting of: third party emergency contact resources, rescue and/or emergency provider networks, and user-defined contacts.

59. The system of claim 58 wherein said messages are sent through communication devices selected from the group consisting of: cellular telephone towers and communication satellites.

60. The system of claim 59 wherein said sensor module and/or said prediction processor generates third and/or prediction signals carrying messages sent to communication satellites via portable satellite communication devices (SPOT).

61. The system of claim 60 wherein said messages generated from said third signals are selected from the group consisting of: (1) a message to the person connected to the sensor that they have been involved in a minor collision event which has been stored in their sensor device, and advising that based on the accumulated collision events they have experienced and making a recommendation as to whether or not they should seek medical attention; (2) a message to the person connected to the sensor that they have been involved in a moderate collision event and advising that and recommending that they see a doctor; (3) a message to a third party emergency contact resource that the person has been involved in a collision event of a specified severity and a message to the person advising that the emergency contact resource has been notified; (4) a message to a rescue and/or emergency provider network that the person has been involved in a collision event requiring emergency response and a message to the person that the rescue/emergency provider network has been notified; and (5) a message to the group tracking and communication device of a monitor that a person was involved in a collision event and making a recommendation as to whether or not the person should receive medical attention.

62. The system of claim 61 wherein said group tracking and communication device is in signal communication with a communication device capable of receiving signals from multiple sensor modules operationally connected to multiple persons or objects, and is capable of sending signals to multiple receivers.

63. The system of claim 11 wherein the group tracking and communication device is in signal communication via the Internet with a processor capable of cloud computing to process and accumulate information selected from a group consisting of demographic information, information on current and previous impact collisions, biological parameters and/or climatic information from single or multiple users, and information about the seriousness and type of previous impact collisions of said persons, and to calculate correlations between injury types and seriousness with the other information, and to predict the seriousness of injury caused by a current collision event from the collected information and correlations.

64. The system of claim 1, wherein the sensor module is operationally connected to a person or object and is capable of determining angular, and optionally direct velocity, of said person or object over time as a result of a collision event and of producing first signals comprising information representing properties of said angular velocity over time, wherein the sensor module comprises one or more components selected from the group consisting of gyroscopes, 3-axis accelerometers, processors, wireless transmitters and data storage buffers.

65. The system of claim 1, wherein the sensor module processor is in signal communication with the sensor module, wherein said sensor module processor is configured to analyze information about measured properties of a collision event received from said sensor module, and compare said information to one or more selected threshold values indicative of the severity of the collision event, and to produce signals comprising information representing the results of said comparisons.

66. The system of claim 65, wherein the sensor module further comprises firmware capable of analyzing and comparing said information and producing said signals.

67. The system of claim 66 wherein said firmware comprises Bluetooth Low Energy to Classic Converter (BLEC) circuitry.

68. The system of claim 66 wherein said firmware comprises Bluetooth Enabled Accelerometer (BEA) circuitry.

69. The system of claim 66, wherein the sensor module is no larger than that of three quarters.

70. The system of claim 66, wherein the sensor module is configured with miniaturized electronic circuitry for converting Bluetooth Low Energy transmission to classic Bluetooth signal wherein said circuitry is capable of being disposed on a component having a size no larger than a quarter.

71. The system of claim 11, wherein the group tracking and communication device further comprises a receiver for receiving signals from two or more sensor modules attached to two or more persons or objects, wherein said signals carry information about measured properties of a collision event occurring to said persons or objects, wherein said group tracking and communication device is programmed to send signals to one or more receivers.

72. The system of claim 71, wherein the group tracking and communication device further comprises at least one wireless transmitter capable of broadcasting low frequency or broadband signals.

73. The system of claim 71, wherein the group tracking and communication device further comprises also comprising a processor and RAM data storage unit.

74. The system of claim 71, wherein the group tracking and communication device further comprises Bluetooth Low Energy to Classic Converter (BLEC) circuitry.

75. The system of claim 71, wherein the group tracking and communication device further comprises Bluetooth Enabled Accelerometer (BEA) circuitry.

76. The system of claim 71, wherein the group tracking and communication device is no larger than a cylinder 25 mm in diameter and 6 mm in height.

77. The system of claim 71, wherein the group tracking and communication device is no larger than a cylinder 10 mm in diameter and 2 mm in height.

78. A method of making a system for sensing, analyzing, and reporting a collision event of a person or object with another person, or object, said method comprising:
providing a sensor module consisting of at least one sensor capable of sensing angular velocity of said person or object over time as a result of said collision event and of producing first signals comprising information representing properties of said angular velocity over time;
operationally connecting said sensor module to one or more persons or objects;
establishing signal communication between said sensor module and a processor programmed to analyze said information and compare it to one or more threshold values indicative of a severity of said collision events and to produce a second signal comprising data representing the results of said comparisons; and
transmitting the second signal produced by said processor to a communication device attached to one or more people or objects and programmed to provide a notification of a severe collision in response to the second signal.

79. The method of claim 78, wherein the method further comprises establishing signal communication between said processor and a group tracking and communication device attached to one or more people or objects and programmed to send signals to one or more receivers.

80. The system of claim 11 wherein said group tracking and communication device comprises at least one wireless transmitter capable of broadcasting low frequency or broadband signals, a processor, and a RAM data storage module.

* * * * *

UNITED STATES PATENT AND TRADEMARK OFFICE
CERTIFICATE OF CORRECTION

PATENT NO.        : 8,860,570 B2                                    Page 1 of 1
APPLICATION NO.   : 13/366097
DATED             : October 14, 2014
INVENTOR(S)       : Thomas et al.

It is certified that error appears in the above-identified patent and that said Letters Patent is hereby corrected as shown below:

On the title page, item [75] the city of residence of inventor Biju Thomas should read "Denver.".

In the Claims

Column 19, line 6, claim 3, the second occurrence of "consisting of" should be deleted.

Column 23, line 42, claim 73, "also comprising" should be deleted.

Signed and Sealed this
Sixteenth Day of June, 2015

Michelle K. Lee
*Director of the United States Patent and Trademark Office*